(12) United States Patent
Bartos

(10) Patent No.: US 8,779,185 B2
(45) Date of Patent: Jul. 15, 2014

(54) PROCESS AND APPARATUS FOR MANUFACTURING PURE FORMS OF AROMATIC CARBOXYLIC ACIDS

(75) Inventor: Thomas M. Bartos, Naperville, IL (US)

(73) Assignee: BP Corporation North America Inc., Houston, TX (US)

(*) Notice: Subject to any disclaimer, the term of this patent is extended or adjusted under 35 U.S.C. 154(b) by 0 days.

(21) Appl. No.: 13/465,807

(22) Filed: May 7, 2012

(65) Prior Publication Data

US 2012/0220800 A1    Aug. 30, 2012

Related U.S. Application Data

(63) Continuation of application No. 11/909,117, filed as application No. PCT/US2006/010255 on Mar. 20, 2006, now Pat. No. 8,173,834.

(60) Provisional application No. 60/663,792, filed on Mar. 21, 2005.

(51) Int. Cl.
*C07C 51/16*    (2006.01)

(52) U.S. Cl.
USPC ........... 562/412; 562/405; 562/407; 562/409; 562/416

(58) Field of Classification Search
None
See application file for complete search history.

(56) References Cited

U.S. PATENT DOCUMENTS

| | | | |
|---|---|---|---|
| 2,833,816 A | 5/1958 | Saffer et al. | |
| 3,584,039 A | 6/1971 | Meyer | |
| 4,286,101 A | 8/1981 | Hashizume et al. | |
| 4,626,598 A | 12/1986 | Packer et al. | |
| 4,629,715 A | 12/1986 | Schroeder | |
| 4,772,748 A | 9/1988 | Hashizume et al. | |
| 4,782,181 A | 11/1988 | James | |
| 4,877,900 A | 10/1989 | Tamaru et al. | |
| 4,892,972 A | 1/1990 | Schroeder et al. | |
| 4,914,230 A | 4/1990 | Abrams et al. | |
| 5,081,290 A | 1/1992 | Partenheimer et al. | |
| 5,103,933 A | 4/1992 | Huff | |
| 5,112,992 A | 5/1992 | Belmonte et al. | |
| 5,175,355 A | 12/1992 | Streich et al. | |
| 5,198,156 A | 3/1993 | Middleton et al. | |
| 5,200,557 A | 4/1993 | Gee et al. | |
| 5,304,676 A | 4/1994 | Hindmarsh et al. | |
| 5,354,898 A | 10/1994 | Schroeder | |
| 5,362,908 A | 11/1994 | Schroeder et al. | |
| 5,463,113 A | 10/1995 | Yamamoto et al. | |
| 5,612,007 A | 3/1997 | Abrams | |
| 5,616,792 A | 4/1997 | Bartos et al. | |
| 5,679,846 A | 10/1997 | Hindmarsh et al. | |
| 5,723,656 A * | 3/1998 | Abrams | 562/412 |
| 5,904,423 A | 5/1999 | Forschner et al. | |
| 6,137,001 A | 10/2000 | Broeker et al. | |
| 6,143,925 A | 11/2000 | Tomitaka et al. | |
| 6,194,607 B1 | 2/2001 | Jhung et al. | |
| 6,504,051 B1 | 1/2003 | Miller, Jr. et al. | |
| 6,852,879 B2 | 2/2005 | Belmonte et al. | |
| 7,135,596 B2 | 11/2006 | Nubel et al. | |
| 7,935,844 B2 | 5/2011 | Bartos | |
| 7,935,845 B2 * | 5/2011 | Bartos et al. | 562/412 |
| 8,173,834 B2 * | 5/2012 | Bartos | 562/412 |
| 2005/0010066 A1 | 1/2005 | Lin | |

FOREIGN PATENT DOCUMENTS

| | | |
|---|---|---|
| EP | 0 498 591 | 8/1992 |
| EP | 0 962 442 | 12/1999 |
| GB | 1373230 | 11/1974 |
| WO | WO 96/11899 | 4/1996 |
| WO | WO 97/27168 | 7/1997 |

* cited by examiner

*Primary Examiner* — Sudhakar Katakam
(74) *Attorney, Agent, or Firm* — Robert N. Carpenter

(57) ABSTRACT

A process and apparatus for manufacture of aromatic carboxylic acids comprises a liquid phase oxidation of aromatic hydrocarbon feed materials and treatment of a high pressure off-gas from the liquid phase oxidation to separate water and reaction solvent and purification of impure aromatic carboxylic acid products wherein a purification liquid includes water from off-gas treatment.

5 Claims, 2 Drawing Sheets

PROCESS AND APPARATUS FOR MANUFACTURING PURE FORMS OF AROMATIC CARBOXYLIC ACIDS

This application is a continuation of U.S. application Ser. No. 11/909,117, filed Sep. 19, 2007, now U.S. Pat. No. 8,173,834.

FIELD OF THE INVENTION

This invention relates to a process and apparatus for manufacture of pure forms of aromatic carboxylic acids by oxidizing aromatic feed material to an impure, crude product in a liquid phase reaction mixture and purifying impure forms of aromatic carboxylic acid, with treatment of off-gas from liquid phase oxidation to recover a liquid comprising water and use of liquid comprising water recovered from oxidation off-gas in purifying impure aromatic carboxylic acid.

BACKGROUND OF THE INVENTION

Terephthalic acid and other aromatic carboxylic acids are widely used in manufacture of polyesters, commonly by reaction with components comprising ethylene glycol, higher alkylene glycols or combinations thereof, for conversion to fiber, film, containers, bottles and other packaging materials, and molded articles.

In commercial practice, aromatic carboxylic acids are commonly made by liquid phase oxidation in an aqueous acetic acid solvent of methyl-substituted benzene and naphthalene feedstocks, in which the positions of the methyl substituents correspond to the positions of carboxyl groups in the desired aromatic carboxylic acid product, with air or another source of oxygen, which is normally gaseous, in the presence of a bromine-promoted catalyst comprising cobalt and manganese. The oxidation is exothermic and yields aromatic carboxylic acid together with by-products, including partial or intermediate oxidation products of the aromatic feedstock, and acetic acid reaction products, such as methanol, methyl acetate, and methyl bromide. Water is also generated as a by-product. Aromatic carboxylic acid, typically accompanied by oxidation by-products of the feedstock are commonly formed dissolved or as suspended solids in the liquid phase reaction mixture and are commonly recovered by crystallization and solid-liquid separation techniques. The exothermic oxidation reaction is commonly conducted in a suitable reaction vessel at elevated temperature and pressure. A liquid phase reaction mixture is maintained in the vessel and a vapor phase formed as a result of the exothermic oxidation is evaporated from the liquid phase and removed from the reactor to control reaction temperature. The vapor phase comprises water vapor, vaporized acetic acid reaction solvent, oxygen gas not consumed in oxidation, gaseous by-products such as methanol, methyl bromide and methyl acetate, carbon oxides and, when the oxygen source for the process is air or another oxygen-containing gaseous mixture, nitrogen, carbon oxides and other inert gaseous components of the source gas.

Pure forms of aromatic carboxylic acids are often favored for manufacture of polyesters for important applications, such as fibers and bottles, because impurities, such as by-products generated from aromatic feedstocks in such oxidation processes and more generally, various carbonyl-substituted aromatic species, are known to cause or correlate with color formation in polyesters made from the acids and, in turn, off color in polyester converted products. Pure forms of aromatic carboxylic acids with reduced levels of impurities can be made by further oxidizing crude products from liquid phase oxidation as described above but at one or more, progressively lower temperatures and oxygen levels, and during crystallization to recover products of the oxidation, for conversion of feedstock partial oxidation products to the desired acid product, as known from U.S. Pat. Nos. 4,877,900, 4,772,748 and 4,286,101. Pure forms of terephthalic acid and other aromatic carboxylic acids with lower impurities contents, such as purified terephthalic acid or "PTA", are made by catalytically hydrogenating less pure forms of the acids, such as crude product comprising aromatic carboxylic acid and by-products generated by liquid phase oxidation of aromatic feedstock, in solution at elevated temperature and pressure using a noble metal catalyst. In commercial practice, liquid phase oxidation of alkyl aromatic feed materials to crude aromatic carboxylic acid and purification of the crude product are often conducted in continuous integrated processes in which crude product from liquid phase oxidation is used as starting material for purification.

The high temperature and pressure vapor phase generated by liquid phase oxidation in such processes is a potentially valuable source of recoverable acetic acid reaction solvent, unreacted feed material, reaction by-products and energy; however, its substantial water content, high temperature and pressure and corrosive nature due to components such as gaseous methyl bromide, acetic acid solvent and water pose technical and economic challenges to separating or recovering components of the off-gas for recycle and recovering its energy content. Further, even minor amounts of impurities that remain unseparated in recovered process streams can prevent re-use of the recovered streams if impurities adversely affect other process aspects or product quality. As described in U.S. Pat. No. 5,200,557, for example, monocarboxylic acids adversely affect hydrogenation catalysts used in purification processes, with even low levels of acetic acid residues such as present in crude aromatic carboxylic acid products recovered from oxidation reaction liquids being considered detrimental.

British Patent Specification 1,373,230, U.S. Pat. Nos. 5,304,676; 5,723,656; 6,143,925; 6,504,051, European Patent Specification 0 498 591 B1 and International Application WO 97/27168 describe processes for manufacture of aromatic carboxylic acids by liquid phase oxidation of aromatic feed materials in which a high pressure off-gas is removed from the oxidation and treated for recovery and recycle of portions or components thereof and, in some cases, recovery of energy. Water recovered from high pressure oxidation off-gases in these processes is generally returned to oxidation with acetic acid condensed from off-gases, recycled to off-gas separations for use as reflux or disposed of in liquid purge streams. Water condensed from oxidation off-gas and then purified by distillation is used to wash a purified terephthalic acid precipitate according to embodiments of U.S. Pat. No. 5,304,676 and treated water condensed from an expanded, low pressure gas after separation of monocarboxylic acid and water vapors in a high pressure oxidation off-gas, catalytic oxidation of a resulting high pressure gas comprising water vapor to remove organic impurities by conversion to water and carbon oxides and expansion of the resulting gas to recover energy is used as a crystallization solvent for purified terephthalic acid according to embodiments of U.S. Pat. No. 5,723,656. However, none of the processes uses liquid condensed from a high pressure off-gas from a liquid phase oxidation as solvent or other liquid comprising water in the purification of impure aromatic carboxylic acids. Further, recoveries of materials and energy from off-gases in such processes often are accomplished at the expense of each other, for example due to loss of energy content on cooling or depressurizing to recover materials, burning of materials to control atmospheric emissions and other losses of oxidation solvent, feedstock and intermediates that result if the high temperature and pressure vapor phase resulting from oxidation is not cooled or depressurized for removal of such materials. Impurities remaining in recycle streams can upset process operation and impair product quality. Added equipment and process steps for recovering materials, energy or both can add further process complexities and limit or preclude their practical utility if they add costs that outweigh materials and energy savings.

Impact of lost energy and materials are magnified by scale of process operations. In world-scale commercial manufacturing plants with annual capacities of 500,000 to 1,000,000 or more tons of product, even fractional percentages or hundreds of parts per million of feedstock and solvent lost or converted to undesired or unusable by-products, minor inefficiencies in energy recovery and incremental additions to effluent water treatment translate to significant practical losses of materials, increases in consumption of fuel or electricity and added processing, as well as unpredictable process efficiencies and economics due to differences and variations in costs for energy, materials and requirements for treatment of gaseous and liquid emissions and effluents.

SUMMARY OF THE INVENTION

This invention provides a process and apparatus which provide or enable manufacture of pure forms of aromatic carboxylic acids with improved recovery and re-use of materials, recovery of energy or both and, in particular, recovery of condensate liquid comprising water from a high pressure off-gas from liquid phase oxidation of aromatic feed materials for use in purification of aromatic carboxylic acid product from liquid phase oxidation or other impure forms of aromatic carboxylic acid.

Among the important features of the invention is the finding that a high pressure vapor phase generated as off-gas or overhead in the liquid phase oxidation of aromatic feed materials to aromatic carboxylic acids can be treated for substantial removal of reaction solvent therefrom in a liquid stream, while a high pressure gas resulting from the separation comprising steam and usually also containing one or more of incondensable components of the oxidation reaction off-gas, unreacted aromatic feed material and reaction by-products, and at least substantially free of solvent monocarboxylic acid, can be processed practically and efficiently at high pressure to recover a liquid which comprises water and is substantially free of organic impurities from the oxidation, such as monocarboxylic acid solvent and its reaction products from oxidation, and is suitable, without need for additional treatment, for use as solvent or other process liquid comprising water in processes for purification of impure aromatic carboxylic acids. Condensate liquid recovered from a high pressure gaseous overhead stream resulting from separation of a high pressure vapor phase from liquid phase oxidation into solvent monocarboxylic acid-rich liquid and a high pressure gas comprising water can replace in whole or in part demineralized or other purified water sources used in known purification processes. One or more of reaction feedstock and by-products from liquid phase oxidation, including by-products of the aromatic feedstock material and of the monocarboxylic acid solvent for oxidation, may also be recovered according to embodiments of the invention. The high pressure vapor phase from liquid phase oxidation also represents a source of recoverable energy and treatment of that vapor phase according to embodiments of the invention allows for the recovery of energy therefrom or from pressurized gases derived therefrom. Energy can be recovered in the form of heat, in the form of work or as both. In some of its embodiments, in addition to providing liquid comprising water suitable for use in purification, for example as solvents for a purification reaction solution or crystallization or recrystallization in recovery of pure forms of product or as wash or seal flush liquids, and the other benefits noted above, the invention can afford surprising flexibility for making a range of pure forms of aromatic carboxylic acids.

In integrated processes for manufacture of pure forms of aromatic carboxylic acids comprising oxidizing aromatic feed material in a liquid phase reaction mixture to crude product comprising aromatic carboxylic acid and oxidation by-products of the feed material, and purifying the crude product by hydrogenation of a solution thereof in a liquid comprising water, the invention can eliminate or reduce requirements for demineralized water or pure water from other sources and provide balance between water generated in the liquid phase oxidation and water consumed in purification not achieved in, and substantially improved over, known processes.

The liquid comprising water that is recovered from the high pressure vapor phase resulting from liquid phase oxidation of aromatic feed materials to aromatic carboxylic acids and used in purification of impure aromatic carboxylic acid according to the invention is recovered from a pressurized gas remaining after substantial separation of solvent monocarboxylic acid and water in a high pressure off-gas from liquid phase oxidation by condensation from the pressurized gas, preferably such that an uncondensed gas remains after the condensation. In a preferred embodiment of the invention, liquid condensate comprising water and substantially free of solvent monocarboxylic acid is recovered by condensation from the pressurized gas by indirect heat exchange to generate steam or another heated heat exchange fluid useful in other steps or processes. An exhaust gas remaining after condensation is under pressure and typically comprises incondensable components of the oxidation reaction off-gas. It may also include minor amounts of aromatic feed material and solvent by-products generated in liquid phase oxidation that pass into the high pressure oxidation overhead. Condenser exhaust gas, while normally under pressure lower than the liquid phase oxidation off-gas, nonetheless is under high pressure and has substantial energy content. Accordingly, the invention in some embodiments provides for recovery of energy from pressurized condenser exhaust gas. Energy can be recovered as heat, work, or a combination thereof.

In some embodiments, the invention also can provide for improved recoveries and re-use of monocarboxylic acid solvent for liquid phase oxidation. In addition to substantial separation of a solvent-rich liquid from oxidation reaction off-gas device and suitability of the solvent-rich liquid for return to or use in oxidation, the invented process includes embodiments that comprise directing to separation as reflux a liquid comprising a purification mother liquor remaining after recovery of a purified aromatic carboxylic acid product from a purification reaction solution. In such embodiments, not only oxidation by-products, for example, carboxybenzaldehyde and toluic acid oxidation intermediates convertible terephthalic or isophthalic acid as desired aromatic acid products, but also solvent monocarboxylic acid, such as solvent residues in the impure aromatic carboxylic acid products used to form purification solutions, or minor amounts of solvent remaining in the liquid condensate comprising water condensed from the pressurized gas from separation, can be returned to oxidation.

Recoveries of solvent monocarboxylic acid, reaction products thereof generated in liquid phase oxidation, unreacted aromatic feed material from the oxidation or combinations thereof present in high pressure vapor phase from oxidation and carried over to a pressurized gas remaining after substantial separation of solvent monocarboxylic acid and water in the vapor phase are further enhanced according to other embodiments in which the pressurized gas is condensed to recover liquid comprising water while leaving a high pressure condenser exhaust gas cooled to a temperature at which one or more scrubbing agents is effective for removing one or more of the feed material, solvent and oxidation by-products of the solvent. The resulting gas can be further treated for separation of feed material and/or such solvent by-products and, in a further embodiment, a stream comprising feed materials, solvent by-products or combinations thereof can be directed to liquid phase oxidation.

In one aspect, the invention provides an apparatus for manufacture of aromatic carboxylic acids. The apparatus affords improved capabilities for recovery of energy and for avoiding materials losses in process operation. In some of its embodiments, the apparatus is configured to provide added benefit by reducing corrosivity of process gas streams, such that components of the apparatus and, in some cases, of auxiliary or other process equipment can be constructed of metals and alloys with moderate corrosion resistance, such as stainless steels, mild steels or duplex steels, as alternatives to titanium, nickel alloy steels and other more expensive, highly corrosion resistant metals conventionally used in aromatic carboxylic acid manufacture.

Briefly, the apparatus according to this aspect of the invention comprises a reaction vessel having a vent for removing reactor overhead vapor; a separation device capable of substantially separating a $C_{1-8}$ monocarboxylic acid gas and water vapors in a high pressure gaseous mixture comprising the monocarboxylic acid and water and in fluid communication with the reaction vessel so as to receive a high pressure vapor phase removed from the reaction vessel; condensing means in fluid communication with the separation device adapted to extract energy from a high pressure gas by condensing at least a portion of the high pressure gas and exchanging heat with a heat sink material; and means for directing a condensate liquid condensed from the high pressure gas to at least one vessel of an apparatus for purifying an aromatic carboxylic acid. A preferred apparatus further comprises an expander in fluid communication with the condensing means. A preferred separation device comprises one or more high pressure distillation columns. Preferably, the condenser is adapted to condense as little as about 20% to about 60% to all or substantially all, of the water present in a high pressure gas stream introduced to the condenser. Optionally, the condenser can be further adapted to return a portion of condensate liquid condensed from a high pressure overhead gas stream to separation.

In somewhat greater detail, the apparatus according to this aspect of the invention comprises a reaction vessel rated for a first pressure and suitable for liquid phase oxidation of an aromatic feed material with gaseous oxygen in a liquid phase reaction mixture comprising monocarboxylic acid solvent and water under conditions effective to maintain a liquid phase reaction mixture and generate a high pressure vapor phase and comprising at least one vent for removing a high pressure vapor phase from the vessel; a separation device rated for a second pressure which is not substantially less than the first pressure and comprising at least one gas inlet in flow communication with the reaction vessel for receiving a high pressure vapor phase removed from at least one vent of the reaction vessel, at least liquid inlet for introducing reflux liquid to the device, at least one gas outlet for removing pressurized gas from the device, at least one liquid outlet for removing a liquid stream from the device and a fractionating zone disposed at a position intermediate at least one gas inlet and at least one gas outlet and capable of substantially separating solvent monocarboxylic acid and water in the high pressure vapor phase gas received in the device such that a liquid stream comprising solvent monocarboxylic acid and substantially free of water and a high pressure gas comprising water and free of substantial solvent monocarboxylic acid are formed; condensing means comprising at least one gas inlet for receiving a high pressure gas removed from at least one gas outlet of the separation device heat exchange means for transfer of heat from a high pressure gas in the condensing means to the heat exchange fluid such that a liquid condensate is condensed from the high pressure gas and a heat exchange fluid at an increased temperature or pressure is formed, at least one outlet for removing from the condensing means a high pressure exhaust gas, and at least one outlet for removing condensate liquid from the condensing means; and means for directing condensate liquid removed from at least one outlet of the condensing means to at least one vessel of an aromatic carboxylic acid purification apparatus. Such and apparatus is preferably adapted for use to carry out purification processes comprising contacting a solution comprising aromatic carboxylic acid and impurities dissolved in a aqueous liquid with hydrogen in the presence of a hydrogenation catalyst at elevated temperature and pressure to form a purification liquid reaction mixture and recovering a solid aromatic carboxylic acid product with reduced impurities from the purification reaction mixture. A preferred apparatus for manufacture of a purified aromatic carboxylic acid by such a process comprises at least one reaction vessel adapted for contacting a liquid purification reaction solution with hydrogen at elevated temperature and pressure in the presence of a hydrogenation catalyst to form a purification liquid reaction mixture and, more preferably, at least one product recovery vessel in flow communication with the reaction vessel for receiving purification liquid reaction mixture removed from the reaction vessel and recovering therefrom solid aromatic carboxylic acid product with reduced levels of impurities. Preferably, such an apparatus also includes one or more additional vessels such as for dissolving crude or impure aromatic carboxylic acid in a purification reaction solvent, filtration or other separation of a solid purified aromatic carboxylic acid from a liquid medium and washing of solid purified aromatic carboxylic acid product.

Apparatus according to an embodiment of this aspect of the invention can also include a power recovery device in fluid communication with the condensing means so as to receive a gas under pressure that exits the condenser through at least one gas outlet. The power recovery device comprises at least one inlet for receiving a gas under pressure and means for extracting work from the high pressure gas.

Another aspect of the invention provides a process for manufacture of aromatic carboxylic acids comprising contacting a feed material comprising at least one aromatic hydrocarbon precursor to the acid with gaseous oxygen in a liquid phase oxidation reaction mixture comprising monocarboxylic acid solvent and water and in the presence of a catalyst composition comprising at least one heavy metal component in a reaction zone at elevated temperature and pressure effective to maintain a liquid phase oxidation reaction mixture and form an aromatic carboxylic acid and impurities comprising oxidation by-products of the aromatic hydrocarbon precursor dissolved or suspended in the liquid phase oxidation reaction mixture and a high pressure vapor phase comprising solvent monocarboxylic acid, water and minor amounts of the aromatic hydrocarbon precursor and by-products; transferring a high pressure vapor phase removed from the reaction zone to a separation zone supplied with liquid reflux comprising water and capable of substantially separating solvent monocarboxylic acid and water in the high pressure vapor phase to form a solvent monocarboxylic acid-rich, water lean liquid and a high pressure gas comprising water vapor; transferring a high pressure gas comprising water vapor removed from the separation zone to a condensing zone and condensing the high pressure gas to form a condensate liquid comprising water and substantially free of organic impurities and a condensing zone exhaust gas under pressure comprising incondensable components of the high pressure gas transferred to the condensing zone; recovering from the condensing zone condensate liquid that comprises water substantially free of organic impurities and is suitable without additional treatment for use as at least one liquid comprising water in a process for purification of aromatic carboxylic acids; and directing condensate liquid comprising water substantially free of organic impurities recovered from the condensing zone to a process for purification of aromatic carboxylic acid, at least one step of which comprises (a) forming a purification reaction solution comprising aromatic carboxylic acid and impurities dissolved of slurried in a liquid comprising water; (b) contacting a purification reaction solution comprising aromatic carboxylic acid and impurities in a liquid comprising water at elevated temperature and pressure with hydrogen in the presence of a hydrogenation catalyst to form a purification liquid reaction mixture; (c) recovering solid purified product comprising aromatic carboxylic acid with reduced levels of impurities from a purification liquid reaction mixture comprising the aromatic carboxylic acid and impurities in a liquid comprising water; and (d) washing with at least one liquid comprising water a solid purified aromatic carboxylic acid product recovered from a purification liquid reaction mixture comprising the aromatic carboxylic acid, impurities and a liquid comprising water; such that a liquid comprising water in at least one step of the purification process comprises the condensate liquid comprising water substantially free of organic impurities.

In another embodiment, a process for manufacture of aromatic carboxylic acid according to the invention comprises, in steps, at least one liquid phase oxidation step comprising contacting a feed material comprising at least one substituted aromatic hydrocarbon in which the substituents are oxidizable to carboxylic acid groups with gaseous oxygen in a liquid phase oxidation reaction mixture comprising monocarboxylic acid solvent and water and in the presence of a catalyst composition comprising at least one heavy metal component in a reaction zone at elevated temperature and pressure effective to maintain a liquid phase oxidation reaction mixture and form an aromatic carboxylic acid and impurities comprising reaction by-products dissolved or suspended in the liquid phase oxidation reaction mixture and a high pressure vapor phase comprising water, monocarboxylic acid, unreacted substituted aromatic hydrocarbon, oxygen and reaction by-products; and at least one purification step comprising contacting with hydrogen at elevated temperature and pressure in the presence of a catalyst comprising a hydrogenation catalyst metal a purification reaction solution comprising a liquid that comprises water and has dissolved therein aromatic carboxylic acid and impurities recovered from the liquid phase oxidation reaction mixture from at least one liquid phase oxidation step to form a purification liquid reaction mixture comprising the aromatic carboxylic acid and hydrogenated impurities dissolved in a liquid comprising water; and at least one off-gas treatment step comprising substantially separating solvent monocarboxylic acid and water in a high pressure vapor phase removed from the reaction zone in at least one liquid phase oxidation step to form a liquid comprising solvent monocarboxylic acid and a high pressure gas comprising water, unreacted feed material, reaction by-products, oxygen and a minor amount of solvent monocarboxylic acid and condensing directly from the high pressure gas a condensate liquid comprising water and substantially free of organic impurities; and at least one step comprising directing condensate liquid comprising water and substantially free of organic impurities condensed from the high pressure gas in at least one off-gas treatment step to at least one purification step such that a liquid comprising water in the purification step comprises the condensate liquid. In more specific embodiments, at least one purification step comprises at least one of the following additional steps in which a liquid comprising water is used: (a) a step comprising suspending or dissolving in a liquid comprising water a solid product comprising aromatic carboxylic acid and impurities recovered from the liquid reaction mixture in at least one liquid phase oxidation step to form the purification reaction solution; (b) a step comprising forming a slurry in a liquid comprising water of a solid product comprising the aromatic carboxylic acid and reduced levels of impurities recovered from the purification liquid reaction mixture; and (c) a step comprising washing with a liquid comprising water a solid product comprising the aromatic carboxylic acid with reduced levels of impurities recovered from the purification liquid reaction mixture.

Liquid phase oxidation, purification and off-gas treatment steps of the process according to embodiments of the invention preferably are integrated such that a liquid phase oxidation product comprising aromatic carboxylic acid and by-products and a high pressure vapor phase from a single liquid phase oxidation are directed to purification and off-gas treatments, respectively, with a liquid condensed from a pressurized gas from the off-gas treatment step being directed to purification for use as a liquid comprising water.

In another embodiment, a process according to the invention comprises in steps, (a) contacting a feed material comprising an aromatic hydrocarbon precursor to the aromatic carboxylic acid and gaseous oxygen in a liquid phase oxidation reaction mixture comprising monocarboxylic acid solvent and water and in the presence of a catalyst composition comprising a heavy metal component in a reaction zone at elevated temperature and pressure effective to maintain a liquid oxidation reaction mixture and to form an aromatic carboxylic acid and impurities comprising reaction by-products dissolved or suspended in the liquid phase oxidation reaction mixture and a high pressure vapor phase that comprises monocarboxylic acid, water, unreacted aromatic hydrocarbon precursor, oxygen gas, and reaction by-products; (b) recovering from the liquid phase oxidation reaction mixture a solid product comprising aromatic carboxylic acid and impurities comprising reaction by-products; (c) suspending or dissolving solid product recovered from the liquid phase oxidation reaction mixture comprising aromatic carboxylic acid and impurities comprising reaction by-products in a liquid comprising water, at least a portion of which comprises a condensate liquid recovered according to step (i), to form a purification reaction solution; (d) contacting the purification solution at elevated temperature and pressure with hydrogen in the presence of a hydrogenation catalyst to form a purification liquid reaction mixture; (e) recovering from the purification liquid reaction mixture a solid purified product comprising aromatic carboxylic acid with reduced levels of impurities and a liquid purification mother liquor comprising water and minor amounts of oxidized aromatic hydrocarbon precursor, hydrogenated derivatives thereof or combinations thereof; (f) transferring a high pressure vapor phase from step (a) comprising solvent monocarboxylic acid, water vapor, unreacted feed material, oxygen and by-products of the liquid phase oxidation reaction to a separation zone supplied with reflux liquid and capable of substantially separating the monocarboxylic acid solvent and water in the high pressure vapor phase; (g) substantially separating solvent monocarboxylic acid and water in the high pressure vapor phase in the separation zone at elevated temperature and pressure into liquid comprising monocarboxylic acid solvent and lean in water and a high pressure gas substantially free of monocarboxylic acid solvent comprising water, aromatic feed material, by-products of the oxidation step and a minor amount of monocarboxylic acid solvent; (h) transferring a high pressure gas removed from the separation zone to a condensing zone and transferring heat between the pressurized gas and a heat exchange fluid to condense from the high pressure gas a condensate liquid comprising water substantially free of organic impurities and form a high pressure condensing zone exhaust gas; and (i) directing at least a portion of the condensate liquid condensed from the pressurized gas in step (h) to step (c).

In more specific embodiments, a liquid stream comprising the solvent monocarboxylic acid-rich liquid from the separation zone is transferred to the reaction zone. In other embodiments, cooling of the high pressure gas transferred to the condensing zone for condensation to recover condensate liquid comprising water substantially free of organic impurities is accomplished by transfer of heat from the high pressure gas to a heat exchange medium to generate steam or another heated fluid under pressure; the resulting steam or heated fluid under pressure can be used for heating in other steps or processes. Exhaust gas from the condensing zone after condensation to recover liquid condensate is under pressure and comprises incondensable components of the high pressure vapor phase removed from a liquid phase oxidation step and directed to separation, and can also contain traces of gaseous solvent monocarboxylic acid, water and aliphatic alcohols and esters formed by side reactions of solvent monocarboxylic acid as a result of the liquid phase oxidation. Accordingly, in other embodiments of the invention, condensation zone exhaust gas can be treated in one or more additional steps for recovery of unreacted feed materials and solvent or solvent by-products of the oxidation step. Alternatively or in addition, energy can be recovered from a condensing zone exhaust gas pressure substantially free of organic impurities, such as by heat exchange to generate steam or another heated fluid for process or other use or by conversion to mechanical energy such as by an expander or other suitable device.

In still further embodiments of the process, at least a portion of the reflux provided to the separation zone for separation of water and solvent monocarboxylic acid in the high pressure vapor phase from a liquid phase oxidation reaction comprises liquid purification mother liquor from purification. In such embodiments of the process, purification of solid product recovered from liquid phase oxidation preferably comprises a further step comprising directing a liquid comprising purification mother liquor to a source of liquid introduced to the separation device as reflux.

BRIEF DESCRIPTION OF THE DRAWING

The invention is described with reference to the Drawing, in which.

DETAILED DESCRIPTION

Figure 1:
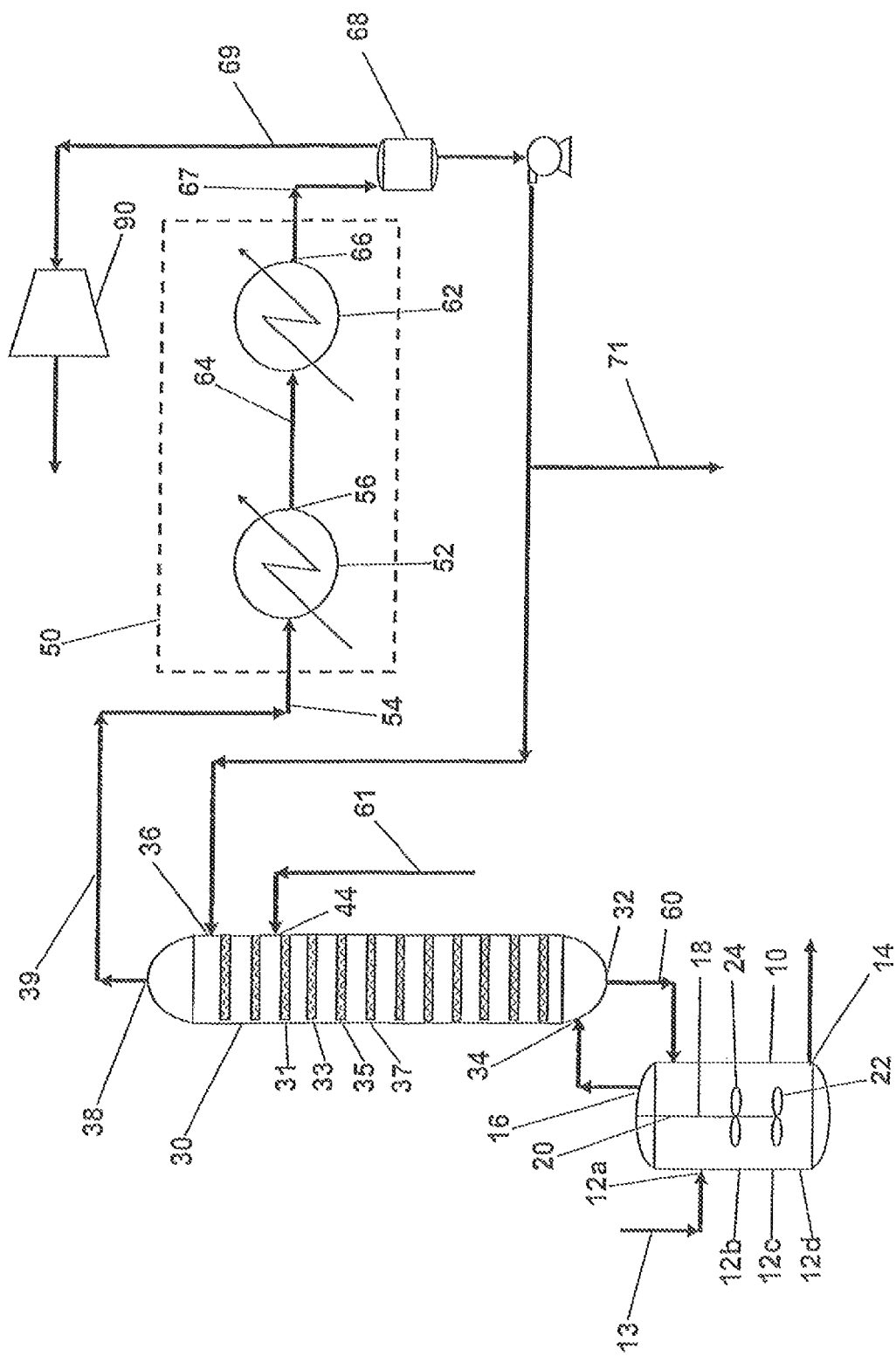
FIG. 1 is a schematic view illustrating embodiments of an apparatus according the invention and useful in the invented processes.

Aromatic carboxylic acids for which the invention is suited include mono- and polycarboxylated species having one or more aromatic rings and which can be manufactured by reaction of gaseous and liquid reactants in a liquid phase system. Examples of such aromatic carboxylic acids include terephthalic acid, trimesic acid, trimellitic acid, phthalic acid, isophthalic acid, benzoic acid and naphthalene dicarboxylic acids. The invention is particularly suited for manufacture of pure forms of terephthalic acid including purified terephthalic acid and so-called medium purity terephthalic acids.

An oxidation step of the invented process is a liquid phase oxidation that comprises contacting oxygen gas and a feed material comprising an aromatic hydrocarbon having substituents oxidizable to carboxylic acid groups in a liquid phase reaction mixture comprising a monocarboxylic acid solvent and water in the presence of a catalyst composition comprising at least one heavy metal component. The oxidation step is conducted at elevated temperature and pressure effective to maintain a liquid phase reaction mixture and form a high temperature, high pressure vapor phase. Oxidation of the aromatic feed material in the liquid phase oxidation step produces aromatic carboxylic acid as well as reaction by-products such as partial or intermediate oxidation products of the aromatic feed material and solvent by-products. The liquid-phase oxidation step and associated process steps can be conducted as a batch process, a continuous process, or a semi-continuous process. The oxidation step can be conducted in one or more reactors.

Suitable aromatic feed materials for the oxidation generally comprise an aromatic hydrocarbon substituted at one or more positions, normally corresponding to the positions of the carboxylic acid groups of the aromatic carboxylic acid being prepared, with at least one group that is oxidizable to a carboxylic acid group. The oxidizable substituent or substituents can be alkyl groups, such as a methyl, ethyl or isopropyl groups, or groups already containing oxygen, such as a hydroxyalkyl, formyl or keto group. The substituents can be the same or different. The aromatic portion of feedstock compounds can be a benzene nucleus or it can be bi- or polycyclic, such as a naphthalene nucleus. The number of oxidizable substituents on the aromatic portion of the feedstock compound can be equal to the number of sites available on the aromatic portion, but is generally fewer than all such sites, preferably 1 to about 4 and most preferably 2. Examples of useful feed compounds, which can be used alone or in combinations, include toluene, ethylbenzene and other alkyl-substituted benzenes, o-xylene, p-xylene, m-xylene, tolualdehydes, toluic acids, alkyl benzyl alcohols, 1-formyl-4-methylbenzene, 1-hydroxymethyl-4-methylben-zene, methylacetophenone, 1,2,4-trimethylbenzene, 1-formyl-2,4-dimethyl-benzene, 1,2,4,5-tetramethyl-benzene, alkyl-, formyl-, acyl-, and hydroxylmethyl-substituted naphthalenes, such as 2,6-dimethylnaphthalene, 2,6-diethylnaphthalene, 2,7-dimethylnaphthalene, 2,7-diethylnaphthalene, 2-formyl-6-methylnaphthalene, 2-acyl-6-methylnaphthalene, 2-methyl-6-ethylnaphthalene and partially oxidized derivatives of the foregoing.

For manufacture of aromatic carboxylic acids by oxidation of their correspondingly substituted aromatic hydrocarbon pre-cursors, e.g., manufacture of benzoic acid from mono-substituted benzenes, terephthalic acid from para-disubstituted benzenes, phthalic acid from ortho-disubstituted benzenes, and 2, 6 or 2,7 naphthalene dicarboxylic acids from, respectively, 2,6- and 2,7-disubstituted naphthalenes, it is preferred to use relatively pure feed materials, and more preferably, feed materials in which content of the pre-cursor corresponding to the desired acid is at least about 95 wt. %, and more preferably at least 98 wt. % or even higher. A preferred aromatic hydrocarbon feed for use to manufacture terephthalic acid comprises para-xylene. A preferred feed material for making benzoic acid comprises toluene.

Solvent for the liquid phase reaction of aromatic feed material to aromatic carboxylic acid product in the liquid phase oxidation step comprises a low molecular weight monocarboxylic acid, which is preferably a $C_1$-$C_8$ monocarboxylic acid, for example acetic acid, propionic acid, butyric acid, valeric acid and benzoic acid. Lower aliphatic monocarboxylic acids and benzoic acid are preferred because they are less reactive to undesirable reaction products than higher molecular weight monocarboxylic acids under reaction conditions used in for liquid phase oxidations to aromatic carboxylic acids and can enhance catalytic effects in the oxidation. Acetic acid is most preferred. Solvents in the form of aqueous solutions thereof, for example about 80 to about 95 wt. % solutions of the acid are most commonly used in commercial operations. Ethanol and other co-solvent materials that oxidize to monocarboxylic acids under the liquid phase oxidation reaction conditions also can be used as is or in combination with monocarboxylic acids with good results. When using a solvent comprising a mixture of a monocarboxylic acid and such a co-solvent, co-solvents oxidizable to the same monocarboxylic are preferably used so that solvent separation steps are not further complicated.

In regard to solvents for the liquid phase oxidation according to the invention, the expression "solvent monocarboxylic acid" as used herein in reference to a component of various gaseous or liquid streams refers to a monocarboxylic acid having the same chemical composition as the monocarboxylic acid used as solvent for the liquid phase oxidation. Such usage also distinguishes those chemical compositions from other monocarboxylic acids that may be present as oxidation by-products. By way of example, when the liquid phase reaction mixture for oxidation includes acetic acid solvent, the expression "solvent monocarboxylic acid" refers to acetic acid but not other monocarboxylic acid species such as benzoic and toluic acids which are common partial or intermediate oxidation by-products of aromatic feed materials used according to the invention. Also, as will be clear from context, the word "solvent" as used in the expression "solvent monocarboxylic acid" may, but does not necessarily, refer to the function of the monocarboxylic acid to which it refers. Thus, again by way of example, "solvent monocarboxylic acid" described as a component of a liquid phase oxidation reaction mixture is present as solvent for the mixture; however, "solvent monocarboxylic acid" described as a component present in a high pressure vapor phase generated in the oxidation or as a component of a liquid phase separated from such a vapor phase is not intended to denote that the monocarboxylic acid is functioning as a solvent.

Catalysts used for the liquid oxidation comprise materials that are effective to catalyze oxidation of the aromatic feed material to aromatic carboxylic acid. Preferred catalysts are soluble in the liquid phase reaction mixture used for oxidation because soluble catalysts promote contact among catalyst, oxygen gas and liquid feed materials; however, heterogeneous catalyst or catalyst components may also be used. Typically, the catalyst comprises at least one heavy metal component such as a metal with atomic weight in the range of about 23 to about 178. Examples of suitable heavy metals include cobalt, manganese, vanadium, molybdenum, chromium, iron, nickel, zirconium, cerium or a lanthanide metal such as hafnium. Suitable forms of these metals include, for example, acetates, hydroxides, and carbonates. Preferred catalysts comprise cobalt, manganese, combinations thereof and combinations with one or more other metals and particularly hafnium, cerium and zirconium.

In preferred embodiments, catalyst compositions for liquid phase oxidation also comprise a promoter, which promotes oxidation activity of the catalyst metal, preferably without generation of undesirable types or levels of by-products. Promoters that are soluble in the liquid reaction mixture used in oxidation are preferred for promoting contact among catalyst, promoter and reactants. Halogen compounds are commonly used as a promoter, for example hydrogen halides, sodium halides, potassium halides, ammonium halides, halogen-substituted hydrocarbons, halogen-substituted carboxylic acids and other halogenated compounds. Preferred promoters comprise at least one bromine source. Suitable bromine sources include bromo-anthracenes, $Br_2$, HBr, NaBr, KBr, $NH_4Br$, benzyl-bromide, bromo acetic acid, dibromo acetic acid, tetrabromoethane, ethylene dibromide, bromoacetyl bromide and combinations thereof. Other suitable promoters include aldehydes and ketones such as acetaldehyde and methyl ethyl ketone.

Reactants for the liquid phase reaction of the oxidation step also include a gas comprising molecular oxygen. Air is conveniently used as a source of oxygen gas. Oxygen-enriched air, pure oxygen and other gaseous mixtures comprising molecular oxygen, typically at levels of at least about 10 vol. %, also are useful. As will be appreciated, as molecular oxygen content of the source increases, compressor requirements and handling of inert gases in reactor off-gases are reduced. When air or other oxygen-containing gaseous mixtures are used as an oxygen source for the process, the high pressure vapor phase generated by the liquid phase reaction in the oxidation step comprises nitrogen or other inert gas components of the oxygen source.

Proportions of aromatic feed material, catalyst, oxygen and solvent are not critical to the invention and vary with factors that include choice of reactants, solvent and catalyst compositions and intended aromatic carboxylic acid product, details of process design and operating factors. Solvent to aromatic feedstock weight ratios ranging from about 1:1 to about 30:1 are preferred, with about 2:1 to about 5:1 being more preferred although higher and lower ratios, even in the range of hundreds to one also can be used. Oxygen gas typically is used in at least a stoichiometric amount based on aromatic feed material but not so great, taking into account reaction conditions, rates and organic components of the high pressure vapor phase resulting from the liquid phase reaction, that a flammable mixture exists in the vapor phase. In commercial operations using preferred aromatic feed materials, solvent monocarboxylic acid, catalyst compositions and operating conditions, oxygen gas, most commonly supplied in the form of air, is preferably supplied to the liquid phase oxidation at a rate effective to provide at least about 3 to about 5.6 moles molecular oxygen per mole of aromatic hydrocarbon feed material. A high pressure vapor phase resulting from liquid phase oxidation is preferably removed from the reaction at a rate such that oxygen content of the vapor phase in a reaction zone contains from about 0.5 to about 8 vol. % oxygen measured on a solvent-free basis. Other things being equal, vapor phase oxygen contents in the lower portion of that range, for example up to about 3 vol. %, favors manufacture of pure forms of aromatic carboxylic acid with somewhat greater impurities contents than at higher vapor phase oxygen contents. For manufacture of pure forms of terephthalic acid by liquid phase oxidation of aromatic precursors such as para-xylene and purification of the resulting liquid phase oxidation product according to the invention, vapor phase oxygen contents of about 0.5 to about 2.5 vol. % are preferred for making so-called medium purity products, in which levels of impurities primarily comprising 4-carboxybenzaldehyde and p-toluic acid range from about 100 to about 1,000 ppmw. Higher vapor phase oxygen contents in the oxidation favor manufacture of products that can be purified to more pure forms of terephthalic acid in which levels of such impurities are generally less than about 200 ppmw. Catalyst suitably is used in concentrations of catalyst metal, based on weight of aromatic hydrocarbon feed and solvent, greater than about 100 ppmw, preferably greater than about 500 ppmw, and less than about 10,000 ppmw, preferably less than about 6,000 ppmw, more preferably less than about 3,000 ppmw. Preferably a halogen promoter and more preferably a promoter comprising bromine, is present. Such a promoter is present in an amount such that the atom ratio of halogen to catalyst metal suitably is greater than about 0.1:1, preferably greater than about 0.2:1 and suitably is less than about 4:1, preferably less than about 3:1. The atom ratio of halogen to catalyst metal most preferably ranges from about 0.25:1 to about 2:1. Other things being equal, reaction rates and consumption of oxygen gas in liquid phase oxidation increase and levels of unreacted oxygen in the vapor phase from oxidation decrease, with increased catalyst concentrations in the oxidation reaction mixture, thereby affording control and flexibility for manufacture of a range of pure forms of aromatic carboxylic acid by the invented process.

The liquid phase reaction for oxidation of aromatic feed material to product comprising aromatic carboxylic acid is conducted in a suitable oxidation reaction zone, which normally comprises one or more oxidation reaction vessels. Suitable oxidation reaction vessels are configured and constructed to withstand the high temperature and pressure conditions and corrosive liquid and vapor phase contents used and present in the reaction zone and to provide for addition and mixing of catalyst, liquid and gaseous reactants and solvent, removal of aromatic carboxylic acid product or a liquid comprising such product for recovery thereof, and removal of a high pressure vapor phase generated by the liquid phase reaction for controlling heat of reaction. Reactor types which can be used include continuous stirred tank reactors and plug-flow reactors. Commonly, oxidation reactors comprise a columnar vessel, normally with a central axis which extends vertically when the vessel is positioned for process use, having one or more mixing features for mixing liquid reactants and distributing oxygen gas within the liquid phase boiling reaction mixture. Typically, the mixing feature comprises one or more impellers mounted on a rotatable or otherwise movable shaft. For example, impellers may extend from a rotatable central vertical shaft Reactors may be constructed of materials designed to withstand the particular temperatures, pressures and reaction compounds used. Generally, suitable oxidation reactors are constructed using inert, corrosion-resistant materials such as titanium or with at least their surfaces that define interior space or volume in which liquid reaction mixture and reaction off-gas are contained lined with materials such as titanium or glass.

A reaction mixture for the liquid phase oxidation is formed by combining components comprising aromatic feed material, solvent and catalyst and adding gaseous oxygen to the mixture. In continuous or semi-continuous processes, components preferably are combined in one or more mixing vessels before being introduced to the oxidation zone; however, the reaction mixture can also be formed in the oxidation zone. The source of oxygen gas can be introduced into the reactor in one or more locations and is typically introduced in such a manner as to promote contact between the molecular oxygen and the other reaction compounds, for example, by introduction of compressed air or other gaseous oxygen source into the liquid body within a lower or intermediate portion of the interior volume of the reaction vessel.

Oxidation of aromatic feed material to product comprising aromatic carboxylic acid is conducted under oxidation reaction conditions effective to maintain a liquid phase reaction mixture and form aromatic carboxylic acid and impurities comprising by-products of the aromatic hydrocarbon precursor dissolved or suspended in the liquid phase reaction mixture and generate a high temperature and pressure vapor phase, gaseous components of which are primarily solvent monocarboxylic acid (i.e., acetic acid when the oxidation reaction solvent is acetic acid) and water. The high pressure vapor phase commonly also comprises unreacted aromatic feed material and oxygen gas that enter the vapor phase and by-products of the liquid phase reaction. When using air, as commonly practiced in commercial scale operations, or other oxygen gas sources comprising nitrogen or other inert gas components, the vapor phase will also comprise those inert components. Heat generated by oxidation is dissipated by boiling the liquid phase reaction mixture and removing an overhead vapor phase from the reaction zone.

Generally temperatures of the liquid phase reaction are maintained at about 120° C. or greater, and preferably at about 140° C. or greater, but less than about 250° C. and preferably less than about 230° C. Reaction temperatures in the range of about 145° C. to about 230° C. are preferred in the manufacture of aromatic carboxylic acid products such as terephthalic acid, benzoic acid and naphthalene dicarboxylic acid. At temperatures lower than about 120° C., the liquid phase oxidation can proceed at rates or with conversions that are economically unattractive or may adversely affect product quality. For example, manufacture of terephthalic acid from para-xylene feedstock at a temperature less than about 120° C. can take more than 24 hours to proceed to substantial completion and the resulting terephthalic acid product can require additional processing due to its impurities content. Temperatures above 250° C. are not preferred due to potential for undesirable burning and loss of solvent. Pressure of the liquid phase reaction mixture can be used to control the temperature at which the liquid phase reaction mixture boils and is selected to maintain a substantial liquid phase reaction mixture. Pressures of about 5 to about 40 kg/cm² gauge are preferred, with preferred pressures for particular processes varying with feed and solvent compositions, temperatures and other factors and more preferably ranging between about 10 to about 30 kg/cm². At a reaction pressure of about 7 to about 21 kg/cm², temperature of a reaction mixture comprising acetic acid as solvent, and of the vapor phase resulting from the liquid phase reaction, is about 170 to about 210° C. Residence times in the reaction vessel can be varied as appropriate for given throughputs and conditions, with about 20 to about 150 minutes being generally suited to a range of processes. For manufacture of some aromatic carboxylic acids, such as manufacture of terephthalic acid from para-xylene feed materials using acetic acid solvent for the reaction mixture, solids contents in the boiling liquid phase reaction mixture can be as high as about 50 wt. % of the liquid reaction mixture, with levels of about 10 to about 35 wt. % being more common. In processes in which the aromatic acid product is substantially soluble in the reaction solvent, solid concentrations in the liquid body are negligible. As will be appreciated by persons skilled in the manufacture of aromatic carboxylic acids, preferred conditions and operating parameters vary with different products and processes and can vary within or even beyond the ranges specified above.

Products of the liquid phase oxidation reaction include aromatic carboxylic acid oxidized from the aromatic feed material, impurities comprising by-products generated as a result of the liquid phase reaction and, as noted above, a high pressure vapor phase that results from the liquid phase reaction, including boiling of the liquid phase reaction mixture to allow removal of the vapor phase for control of reaction temperature. Specific examples of by-products of the aromatic feed material include partial or intermediate oxidation products such as toluic acids, tolualdehydes, carboxybenzaldehydes and hydroxymethyl benzoic acids. By-products of the liquid phase reaction also include solvent reaction products such as methanol and other lower aliphatic alcohols oxidized from the reaction solvent and esters generated by reaction of such alcohols with the solvent, examples of which include methyl acetate, methyl propionate, methyl butyrate and the like. By-products commonly are present in both the liquid phase oxidation reaction mixture and the vapor phase resulting therefrom. Carbon oxide by-products can result from oxidation of solvent, feed materials or their by-products. In embodiments of the invention in which the liquid phase reaction is conducted using a source of bromine as promoter, by-products also typically include lower alkyl bromides, e.g., methyl bromide when using acetic acid as the reaction solvent, which commonly forms by reaction of bromide ions with acetic acid. As above, these bromine-containing by-products and impurities may be present in one or both of the liquid phase reaction mixture and the high pressure vapor phase generated therefrom. In some embodiments of the invented process, for example those in which solid product from liquid phase oxidation is purified and a mother liquor or other recycle streams comprising purification step liquids or components thereof are transferred directly or indirectly to a liquid phase oxidation, by-products such as toluic acids carried over into purification liquids as well as hydrogenated derivatives of various by-product compounds resulting from purification steps also may be present in the liquid phase reaction mixture.

Water also is produced as a by-product of the liquid phase reaction in the oxidation step. However, because water may also be present in the liquid phase reaction mixture as a result of addition thereto, for example when using aqueous monocarboxylic acid solvents or in recycle streams from other process steps, and also due to the significant amounts of water present in the oxidation step, whether as by-product or deliberate addition, and inability or lack of need to distinguish between water of reaction and water added deliberately, the expression "by-products of the liquid phase reaction" and like expressions used herein do not refer to water unless stated otherwise. Similarly, when water or water vapor is described herein as a component of various process liquids, gases or streams, it is without regard to whether the water is by-product water from liquid phase oxidation, deliberately added in the process or both unless otherwise stated or clear from context.

Aromatic carboxylic acid reaction product slurried or dissolved in a portion of the liquid reaction mixture from the liquid phase oxidation can be treated using conventional techniques to recover aromatic carboxylic acid reaction product contained therein. Typically, aromatic carboxylic acid product and by-products of the aromatic feed material to oxidation slurried, dissolved or slurried and dissolved in liquid reaction mixture are removed from the reaction zone used for the liquid phase reaction and recovered by suitable techniques. Thus, liquid phase oxidation according to invented process can comprise, in addition to the oxidation reaction step, a step comprising recovering from a liquid phase oxidation reaction mixture a product comprising aromatic carboxylic acid and impurities comprising reaction by-products. The product preferably is recovered as a solid product.

Soluble product dissolved in the liquid can be recovered by crystallization, which usually is accomplished by cooling and releasing pressure on a liquid slurry or solution from the oxidation reaction zone. Solid product slurried in the liquid and solids crystallized from reaction liquid or from crystallization solvents are conveniently separated from the liquids by centrifuging, filtration or combinations thereof. Solid products recovered from the reaction liquid by such techniques comprise aromatic carboxylic acid and impurities comprising by-products of the aromatic feed material. Liquid remaining after recovery of solid product from the liquid reaction mixture, also referred to as oxidation mother liquor, comprises solvent monocarboxylic acid, water, catalyst and promoter, soluble by-products of the liquid phase oxidation and impurities that may be present such as from recycle streams. The mother liquor normally also contains minor amounts of aromatic carboxylic acid and partial or intermediate oxidation products of the aromatic feed material remaining unrecovered from the liquid. The mother liquor is preferably returned at least in part to the reaction zone of at least one liquid phase oxidation so that components thereof that are useful in the liquid phase reaction, such as catalyst, promoter, solvent and by-products convertible to the desired aromatic carboxylic acid are re-used.

In preferred embodiments of the invention, a liquid phase reaction mixture from oxidation comprising aromatic carboxylic acid and by-products of a liquid phase oxidation reaction is recovered from the liquid by crystallization in one or more stages, such as in a single crystallization vessel or a series of crystallization vessels, with sequential reductions in temperature and pressure from earlier to later stages to increase product recovery. Crystallization in two to four stages, for example from an oxidation reaction temperature in the range of about 140 to about 250° C. and pressure in the range of about 5 to about 40 kg/cm$^2$ gauge to a final crystallization temperature in the range of about 110 to about 150° C. and pressure of ambient to about 3 kg/cm$^2$, provides substantial crystallization of solid aromatic acid product. Mother liquor separated from the solid product by crystallization can be returned to the liquid phase reaction as described above. Heat is removed from the vessels used for crystallization by removal of a gas phase formed as a result of flashing or other pressure letdown of the reaction liquid, with a vapor phase removed from one or more stages preferably condensed and, directly or indirectly through one or more additional recovery stages, as discussed below, returned at least in part to the reaction zone for use in liquid phase oxidation.

Solid product recovered from the liquid phase oxidation, typically comprising aromatic carboxylic acid and impurities comprising oxidation by-products such as intermediate oxidation products of the aromatic feed material, can be separated from liquid oxidation mother liquor resulting from recovery of the solid product by any suitable technique. Examples include centrifuging, vacuum filtration, pressure filtration and filtration using belt filters. The resulting solid product is preferably washed after separation with liquid comprising water such as pure water or a wash liquid comprising minor amounts of solvent monocarboxylic acid, catalyst, aromatic feedstock, oxidation by-products or combinations thereof that can be beneficially recycled to oxidation, either directly or combined with other liquids such as oxidation mother liquor recycle or other liquids returned to the reaction zone. Separation of solid impure aromatic carboxylic acid recovered from an oxidation mother liquor and washing of solid product can be conveniently accomplished by solvent exchange filtration under pressure using pressure filters such as are disclosed in U.S. Pat. No. 5,679,846, and U.S. Pat. No. 5,200,557. A preferred filtration device for such separations is a BHS Fest filter as described more fully in U.S. Pat. No. 5,200,557. Mother liquor and wash liquids removed from the filtered cake can be transferred directly or indirectly to liquid phase oxidation. Filtration and washing of the solid product in multiple stages and with increasingly pure wash liquids, for example liquids removed from filter cake in downstream stages as wash liquid in prior stages, can provide additional benefit by concentrating solvent monocarboxylic acid displaced from filtered solids for return to oxidation. In a more specific embodiment, the filtered cake wet with wash liquid resulting from such positive displacement filtration is directed from a final wash stage to a drying stage wherein it is optionally contacted with inert gas, typically under light to moderate pressure, for substantial removal of residual liquid from the cake. After washing and substantial removal of wash liquid from solid product comprising aromatic acid and by-products, the resulting solid can be dried and directed to storage or other steps, which may include preparation of a reaction solution for purification of the solid product. Preferably, levels of residual solvent monocarboxylic acid in solid product directed to purification are about 5,000 parts per million by weight ("ppmw") or less. Solid product can be dried with a flowing stream of nitrogen or other inert gas to reduce residual solvent levels.

In addition to the aromatic carboxylic acid reaction product formed in the liquid phase reaction of an oxidation step according to the invented process, a high pressure vapor phase is generated, comprising solvent monocarboxylic acid and water and usually also comprising by-products of the liquid phase oxidation and unreacted aromatic feed material and oxygen gas and, if present, inert components of the oxygen source, as described above. Temperature and pressure of the vapor phase present in the reaction zone corresponds to conditions of the liquid phase reaction. An off-gas treatment step according to the invention provides for recoveries of energy, materials and combinations thereof.

An off-gas treatment step of the invented process comprises substantially separating solvent monocarboxylic acid and water vapors from a stream comprising a high pressure vapor phase that is removed from at least one liquid phase oxidation step such that at least one solvent monocarboxylic acid-rich liquid phase and at least one high pressure gas comprising water and typically also comprising unreacted feed material, reaction by-products, oxygen and a minor amount of solvent monocarboxylic acid are formed and condensing directly from the high pressure gas a condensate liquid comprising water and substantially free of organic impurities such as solvent monocarboxylic acid, unreacted aromatic feed material to liquid phase oxidation and oxidation by-products of the feed material. Separation is conducted with the high pressure vapor phase at a temperature and under pressure not substantially less than temperature and pressure of the vapor phase in the liquid phase oxidation step from which the vapor phase is removed. The off-gas treatment preferably comprises steps that comprise transferring a high pressure vapor phase from at least one liquid phase oxidation step as described above comprising gaseous solvent monocarboxylic acid and water, and usually also comprising unreacted feed material, oxygen and by-products of the oxidation step to a separation zone supplied with reflux liquid and capable of substantially separating the solvent monocarboxylic acid and water in the high pressure vapor phase, substantially separating solvent monocarboxylic acid and water in the high pressure vapor phase in the separation zone at elevated temperature and pressure into a liquid phase, which is rich in solvent monocarboxylic acid, lean in water and can also comprise components of the high pressure vapor phase less volatile than the solvent monocarboxylic acid, and a high pressure gas substantially comprising water vapor and substantially free of solvent monocarboxylic acid and other organic impurities such as unreacted aromatic feed materials and its by-products from oxidation, transferring high pressure gas removed from the separation device to a condensing zone to condense from the high pressure gas a liquid condensate comprising water substantially free of organic impurities. Condensation preferably is conducted by transferring heat between the high pressure gas and a heat exchange fluid.

In greater detail, separation according to an off-gas treatment step according to the invention comprises directing a high pressure vapor phase removed from the reaction vessel used for liquid phase oxidation to a separation zone that is capable of operating with the vapor phase at high temperature and pressure to substantially separate water and solvent monocarboxylic acid in the vapor phase. The high pressure vapor phase can be transferred from the reaction zone of a liquid phase oxidation to the separation zone directly, as where a separation device is mounted directly or in close association with an oxidation reaction vessel or other reaction zone, or indirectly, for example by means suitable conduits, valves, pumps and the like for effecting transfer. A minor portion of the high pressure and high temperature vapor phase from the liquid phase oxidation may be directed to other uses, such as generation of high pressure steam or heat exchange fluid. Preferably, the vapor phase transferred to the separation device remains at high enough temperature and pressure so that energy content of the vapor phase entering the separation device is at least substantially retained and the vapor phase provides sufficient heat for separation in contact with reflux liquid supplied to the separation zone. Most preferably, transfer of the vapor phase to the separation zone is achieved by passage directly from the reaction zone or through suitable pressure rated piping such that temperature of the vapor phase entering the separation zone is no more than about 10° C. cooler than the reaction temperature in the liquid phase oxidation and pressure of the vapor phase entering the separation zone is no more than about 3 $kg/cm^2$ less than the pressure in the liquid phase oxidation. The separation zone also is designed for operation at high temperature and pressure, and preferably at temperatures and pressures not substantially less than the temperature and pressure of the high pressure vapor phase present in the reaction zone to avoid loss of energy content of the vapor phase from the reaction zone. More preferably, the separation zone is designed for treating a vapor phase under pressure of at least about 80%, more preferably at least about 90%, and still more preferably at least about 95%, of the pressure of the vapor phase in the oxidation step. Pressure rating of equipment of the separation zone preferably is at least about 80%, more preferably about 90 to about 110%, of the rating of the oxidation reaction vessel or zone of the oxidation step of the invented process from which the vapor phase is directed to separation.

The separation zone preferably is capable of substantially separating solvent monocarboxylic acid and water vapors in the high pressure vapor phase introduced to separation such that a high pressure gas resulting from the separation contains no more than about 10%, and more preferably no more than about 5% of the solvent monocarboxylic acid content of the vapor phase introduced to the separation zone. More preferably, solvent monocarboxylic acid content of the high pressure gaseous effluent from separation is no more than about 2%, and still more preferably no more than about 1%, of the solvent monocarboxylic acid content of the vapor phase introduced to the separation zone.

The separation zone for off-gas treatment according to the invention can comprise any device suitable for substantially separating solvent monocarboxylic acid and water in the high temperature and pressure vapor phase removed from the liquid phase oxidation into a vapor phase flow through the device at high temperature and pressure to obtain a liquid phase rich in solvent monocarboxylic acid and a pressurized gas comprising water, as described above. Preferred separation devices are various columns or towers, often referred to as distillation columns and towers, dehydration towers, rectifying columns, water removal columns and high efficiency separation devices, that are designed for contact between gas and liquid phases flowing therethrough for mass transfer between the phases in a plurality of theoretical equilibrium stages, also sometimes referred to as "theoretical plates," such that the gas phase is separated or apportioned into fractions with various boiling ranges such that a liquid phase rich in at least one higher boiling component, such as the solvent monocarboxylic acid in the invented process, condenses from the vapor phase leaving a gas substantially depleted of such higher boiling component an comprising one or more lower boiling species, such as the water of the oxidation vapor phase in the invented process. Temperature of the high pressure vapor phase removed from oxidation normally is high enough that there is no need for reboiling capability beyond that provided by the liquid phase oxidation reaction. Countercurrent flow of gas and liquid phases, such as by introducing a gas phase at a lower portion of the device and reflux liquid at an upper portion, is preferred for promoting contact between gas and liquid phases in the separation device. Contact also is promoted by internal structure providing surface for gas-liquid contact.

The separation zone according to the invention can comprise a single device or multiple devices, such as towers, columns or other structure, in series. When using two or more devices in series, they are configured, and their respective inlets and outlets communicate such that high pressure vapor phase removed from the oxidation reaction vessel flows into vapor phase flow through the series with separation therein of water and $C_{1-8}$ monocarboxylic acid in the high pressure vapor and reverse flows of liquid, including reflux and solvent monocarboxylic acid-rich liquid separated from the high pressure vapor phase, within or between devices such that liquid rich in solvent monocarboxylic acid but lean in water can be withdrawn, preferably from a first device in the series and a high pressure gas from the separation comprising water vapor and substantially free of organic impurities can be removed, preferably from the last device in the series.

Vapor phase removed from the liquid phase oxidation reaction zone is directed to the separation zone maintained under conditions such that temperature and pressure of the vapor phase introduced to the device are not substantially reduced relative to inlet temperature and pressure as describe above. Temperatures of the vapor phase in the separation zone preferably range from about 140 to about 200° C. and more preferably from about 160 to about 185° C. Pressures from about 5 to about 40 kg/cm$^2$ are preferred, with about 10 to about 20 kg/cm$^2$ being more preferred.

Reflux liquid comprising water is supplied into contact with the high pressure vapor in the to the separation zone. Any suitable source of liquid comprising water and substantially free of impurities detrimental to separation can be utilized. Preferred sources of reflux liquid include liquids condensed from high pressure gases removed from separation and/or condensing zones according to the invented process. In another preferred embodiment described more fully herein, purification mother liquor obtained in recovery of a purified aromatic carboxylic acid product from at least one purification liquid reaction mixture is directed to separation such that reflux to the separation comprises the purification mother liquor. Most preferably, reflux liquid for separation comprises such a purification mother liquor and liquid comprising water condensed from high pressure gases removed from separation and/or condensing zones according to the invention, which may be supplied to separation individually or combined in one or more individual streams.

Reflux liquid preferably is supplied at a rate and temperature effective to quench heat of the liquid phase oxidation reaction transferred to the separation zone in the vapor phase from the oxidation. When the separation zone is coupled to a reaction vessel from liquid phase oxidation for substantially direct transfer of vapor phase from oxidation to separation, the reaction vessel functions as a reboiler. In such embodiments, the rate at which liquid reflux is supplied to the separation zone is conveniently expressed as weight of liquid provided to the zone relative to weight of aromatic feed material introduced to the liquid phase oxidation. Preferably, reflux liquid provided to the separation zone according to the invented process is at a temperature in the range of about 120 to about 170° C. and more preferably at about 130 to about 160° C. At such temperatures, liquid preferably is supplied to separation at a rate of about 4 to about 5 weights of the liquid per weight of aromatic precursor introduced to the liquid phase oxidation.

Water and solvent monocarboxylic acid vapors contained in the high pressure vapor stream removed from a liquid phase oxidation step and introduced into the separation zone are separated such that a solvent monocarboxylic acid-rich liquid phase which is lean in water condenses from the high pressure vapor stream and a high pressure gas comprising water and substantially depleted of solvent and higher boiling components remains. The separated liquid phase preferably comprises at least about 60 wt. % solvent monocarboxylic acid and no more than about 35 wt % water. More preferably, water content of the separated liquid phase is about 15 to about 30 wt %. The liquid stream from separation typically also contains minor amounts of heavier impurities, such as minor amounts of aromatic carboxylic acid product and partial or intermediate oxidation by-products of the aromatic feed material, such as benzoic acid and, depending on aromatic precursor used in the oxidation, m-toluic acid and/or p-toluic acid, and may also include other components, such as catalyst metals and hydrogenated oxidation by-products introduced from streams recycled, for example to oxidation or as reflux liquid to separation, from other process steps. Content of such heavier components preferably is no more than about 1 wt. %.

The solvent monocarboxylic acid-rich liquid phase condensed from the vapor phase in the separation zone is a valuable source of solvent for liquid phase oxidation. As described above, it also may include oxidation by-products of the aromatic feed material and other components suitable for being returned to oxidation and converted to the desired aromatic carboxylic acid. Other suitable uses for the liquid condensate include wash liquids for rotary vacuum filters or other devices used for solid-liquid separations of recovered solid products of a liquid phase oxidation from oxidation mother liquors or crystallization solvents and make up to scrubbers, such as oxidation dryer scrubbers if used in the process. In a preferred embodiment of the invented process, at least a portion, and, more preferably, all or substantially all of the separated liquid phase condensed from the high pressure vapor phase introduced to the separation zone is returned to liquid phase oxidation, either directly to a reaction vessel or to holding vessels used for supply of makeup solvent to a reaction zone. In such embodiments, water and solvent monocarboxylic acid in the high pressure vapor phase introduced to the separation zone are preferably separated such that a liquid phase resulting from the separation contains about 15 to about 30 wt. % water and, more preferably, such that water content of the separated liquid together with water returned to oxidation in other liquid streams from the process are substantially balanced with water vapor removed from oxidation in the high pressure overhead vapor phase and liquid water removed from oxidation for recovery and separation of aromatic carboxylic acid product of the oxidation.

The high pressure gas resulting from separation comprises a substantial volume of water and is relatively free of solvent monocarboxylic acid. Preferably the gas comprises at least about 55 vol. %, and more preferably at least about 65 vol. %, water. Solvent monocarboxylic acid content of the gas is generally less than about 5 and preferably less than about 3 wt %. Typically, the pressurized gas also contains unreacted aromatic feed material and by-products of the liquid phase oxidation, typically in amounts ranging up to about 1 wt %. Oxygen gas content of the pressurized gas from separation typically ranges up to about 4 vol. %, preferably from about 1 to about 4 vol. %. Inert gas components of the oxygen source, which typically include nitrogen and carbon oxides, can constitute up to about 45 vol. % of the pressurized gas; when using air as a gaseous oxygen source, nitrogen content of the pressurized gas typically ranges from about 30 to about 40 vol. %.

Generally, pressure of the gas resulting from the separation is up to about 1 $kg/cm^2$ gauge less than the pressure in the liquid phase oxidation reaction. Temperature of the high pressure gas from separation is up to about 20° C. less than the temperature of the liquid phase oxidation reaction, and preferably about 5° C. to about 15° C. less than the oxidation reaction temperature. Preferably, the high pressure gas from the separation is at a temperature greater than about 100° C., more preferably greater than about 120° C., and less than about 250° C., more preferably less than about 230° C. Pressure of the pressurized gas remaining after the separation is about 4 to about 40 $kg/cm^2$ gauge.

High pressure gas removed from the separation zone after substantial separation of water and solvent monocarboxylic acid in the high pressure vapor phase from oxidation is directed continuously to a condensing zone for condensing from the gas a liquid condensate comprising water substantially free of organic impurities such as solvent monocarboxylic acid and by-products of the aromatic feed material and solvent from oxidation. The condensing zone can comprise any means effective for condensing water substantially free of organic impurities from the high pressure gas introduced to the condensing zone. Preferably, it includes one or more condenser or heat exchange means effective for providing indirect heat transfer between the high pressure gas and a heat sink material, and preferably a heat exchange fluid. A single device or a plurality of devices in series can be employed. Shell and tube heat exchangers and kettle type condensers are examples of preferred devices. Preferably, all or substantially all of the high pressure gas from separation is directed to the condensing zone to enable substantial recovery of both energy and materials therefrom. Cooling preferably is conducted under conditions such that a condensing zone exhaust gas under pressure not substantially reduced from that of the high pressure gas introduced to the condensing zone remains after condensing the liquid condensate and is withdrawn from the condensing means. That pressurized condensing zone exhaust gas comprises incondensable components of the high pressure gas from the separation zone, gaseous reaction by-products and minor amounts of aromatic feed material and most preferably is at a temperature of about 50 to about 150° C. and under pressure that is no more than about 3 $kg/cm^2$ less than the pressure of the inlet gas to the condensing zone. More preferably, the pressure differential between a gas removed from the separation device and the condensing zone exhaust gas after condensation of liquid condensate is about 2 $kg/cm^2$ or less and most preferably about 0.5 to about 1 $kg/cm^2$.

Cooling of high pressure gas by heat exchange with a heat sink material in the condensing zone also serves to heat the heat sink material. The heat sink material preferably is a heat sink fluid, and most preferably water. When using water as the heat exchange fluid, heat exchange with the high pressure gas from separation converts the water to steam which can be directed to other parts of the invented process for heating or to uses outside the process. Similarly, heat exchange between the pressurized gas and liquids from other process steps can be used for heating such liquids. In a preferred embodiment of the invented process, heat exchange between the high pressure gas from the separation zone introduced to the condensing zone and heat exchange fluid comprising water is conducted in a series of heat exchangers operated at successively cooler temperatures such that steam at different pressures is generated from the heat exchange water. Steam at different pressures is preferably directed to one or more process steps in which steam under corresponding pressure or pressures is useful for heating, while liquid condensate comprising water at successively lower temperatures is generated from the pressurized gas.

Energy can be recovered from exhaust gas from the condensing zone in the form of heat, in the form of work or as both. Recovering energy as heat for the process can reduce consumption of fuel that would otherwise be needed to generate heat for the process. Energy recovered as work can be converted to electricity for use in the process, thereby reducing consumption of electricity from external sources if used in the process.

While preferred embodiments of the invention comprise condensing all or substantially all of the high pressure gas transferred to the condensing zone, in some embodiments of the invention, condensation of high pressure gas removed from the separation zone is conducted by extracting heat energy from the gas such that only a portion of the water content of the gas is condensed. The effectiveness of heat exchange as an energy recovery method decreases as additional increments of water are condensed. Accordingly, partial condensation may be used in embodiments of the invention to increase total energy recovery, though usually with lower materials recovery than in other embodiments, by avoiding the range in which the efficacy of heat exchange is substantially reduced. Partial condensation allows recovery of a liquid condensate comprising substantially pure water with low organic impurities content and recovery of heat energy transferred to a heat exchange fluid on cooling of the high pressure gas to condense the liquid condensate, while also leaving uncondensed water in a high pressure condensing zone exhaust gas for further energy recovery in the form of work.

In embodiments of the invention in which high pressure gas directed to the condensing zone is subjected to condensation so that its condensable components are not fully condensed, the partial condensation is preferably conducted so that about 50 to about 85% of the water content of the inlet high pressure gas to the condensing zone is condensed. Most preferably, in such embodiments, about 70 to about 80% of the water content of the inlet pressurized gas is removed by the condensation. The exhaust gas in such embodiments is suitable for extraction of energy in the form of heat, such as by heat exchange, or as work, such as with an expander.

According to other embodiments of the invention, all or substantially all of a high pressure gas from separation of monocarboxylic acid and water in the high pressure vapor phase from oxidation is condensed by heat exchange with a heat sink fluid. Condensation of all or substantially all of the condensable components of the high pressure gas from separation reduces the volumetric flow of gas remaining after condensation to subsequent processing steps and permits use of metals with only low or moderate corrosion resistance, such as stainless steels, mild steels or duplex steels, as alternatives to more expensive, highly corrosion resistant metals or alloys in equipment for subsequent off-gas treatment steps that may be included in the process. Substantially complete condensation of condensable components of a high pressure gas removed from separation also increases the volume of liquid condensate comprising water substantially free of organic impurities generated according to the invented process and can facilitate enhanced recovery of aromatic feed material and solvent monocarboxylic acid or liquid phase oxidation by-products thereof remaining in uncondensed gases remaining after condensation.

Condensation can be conducted in a single step. It also can be conducted in multiple steps in which a gas stream comprising high pressure gas removed from a separation zone is cooled to a first temperature in a first stage to yield a first stage condensate liquid and an uncondensed portion of the gas which is subsequently condensed at a lower temperature in a second stage to provide a second stage condensate liquid and an uncondensed portion of the gas introduced to the second stage, and optionally one or more additional stages in which an uncondensed portion of gas from a prior stage is condensed at a lower temperature than in the previous stage to form a liquid condensate and a remaining uncondensed gaseous portion. Heat exchange between the pressurized gas and uncondensed portions thereof in the staged condensers provides heat exchange fluid at different temperatures or pressures, for example moderate and low pressure steam, which can be used for heating in other process steps or outside the process. In preferred embodiments of the invention, two or more levels of steam are produced for energy recovery, which is conveniently accomplished using a condensing or other low pressure steam turbine. In such embodiments, condensate liquid removed at different temperatures can be directed to other process uses with corresponding temperatures, thereby avoiding additional heating or cooling of the condensate portions and, in some cases, limiting buildup of certain impurities in steps to which condensate liquids are recycled. For example, condensate liquids removed at temperatures in the range of about 90 to about 130° C. can be directed preferentially to use in one or more steps of a purification process such as mixing impure aromatic carboxylic acid in liquid comprising water to form a purification reaction solution or as crystallization solvent for purified aromatic carboxylic acid products. Condensate liquids recovered at higher temperatures, for example in the range of about 130 to about 160° C., are well suited, with little or no additional heat input, as reflux to separation as such or in combination with aqueous liquids from other process steps such as mother liquor remaining after recovery and/or separation of purified aromatic carboxylic acid in a purification step. Such high temperature condensate liquids can provide additional benefit when used as reflux to separation due to their lower content of light components, such as lower alcohols and solvent monocarboxylic acid esters thereof that are generated as solvent by-products in liquid phase oxidation and tend to condense in greater concentrations in lower temperature condensate liquids. Lower temperature condensates, for example those in the range of about 60 to about 90° C., are also well suited for hot condensate uses such as wash liquids for product separations and seal flush liquids in liquid phase oxidation, purification or both, and still cooler condensate, for example in the range of about 40 to about 50° C., for cold condensate uses such as scrubber washes. While condensation at different temperatures such that condensate liquid can be directed to other process uses with compatible temperatures provides options for favorable energy management in the invented process, it will be appreciated that liquid condensate portions or streams condensed at higher or lower temperatures than may be needed or preferred for use in other steps can be cooled or heated as may be desired, for example by heat exchange, for use in such other steps.

Exhaust gas from the condensing zone is under pressure and, while substantially free of water vapor according to preferred embodiments of the invention, can retain a portion of the water from the pressurized gas from separation depending on the extent of condensation in the condensation step. In addition to such water vapor as may be present in the exhaust gas, the gas can comprise incondensable components from the liquid phase oxidation off-gas, such as unreacted oxygen from oxidation, nitrogen, carbon oxides and other inert gas components if present in the oxygen source for oxidation, and carbon oxides and minor amounts of other oxidation by-products of the feed material and of the solvent monocarboxylic acid, unreacted feed material and traces of solvent monocarboxylic acid from the off-gas not removed in other steps. Even when water in the exhaust gas is substantially completely condensed into the liquid condensate, such that the uncondensed exhaust gas remaining after condensation is substantially free of water, pressure of the exhaust gas is also sufficiently high and, especially when the gaseous oxygen source for liquid phase oxidation is air or another gaseous mixture with significant inert gas content such that the vapor phase removed from oxidation and, in turn, pressurized gases from the separation and condensing zones contain substantial inert gas content, volume of the condensing zone exhaust gas is such that it can be a useful source for recovery of energy.

According to some embodiments of the invention, energy is recovered from the pressurized exhaust gas from condensation. Preferably, energy is recovered in the form of work. In these embodiments, a pressurized gas stream comprising exhaust gas from the condensing zone is transferred, directly or indirectly, to a device for recovering energy as work. A preferred energy recovery device is an expander or similar apparatus adapted to receive a flow of gas under pressure and equipped with blades capable of being rotated by the flowing gas, thereby generating work useful in other process steps or outside the process and a cooled gas under reduced pressure. Work extracted from the pressurized gas can be used, for example, to generate electricity using a generator or for operating a compressor used to compress air or sources of gaseous oxygen used in liquid phase oxidation or other equipment requiring mechanical work. Such extracted energy can be used elsewhere in the process or in other processes. Alternatively, it can be stored or delivered to an electrical grid for transmission to other locations. Exhaust gas remaining after recovery of energy as work can be vented, preferably after being subjected to additional treatments, for example condensation to remove water if present in appreciable amounts in the condensing zone exhaust gas, and caustic scrubbing to remove bromine or other compounds which may be undesirable for atmospheric release. If desired, energy recovery can be conducted after scrubbing or otherwise treating the gas for removal of corrosive components. Removal of corrosive components before recovery of energy can be beneficial in allowing internal components of an expander or other power recovery device to be constructed of less corrosion-resistant materials than might otherwise be preferred; however, treatment for removal of such components also can reduce power recoverable from the gas.

As an alternative to recovering energy from a condensing zone high pressure exhaust gas or, more preferably, as an additional step preceding recovery of energy as in the form of work as described above, exhaust gas from condensation can be treated for removal of organic and other combustible compounds and corrosive components. Such treatments, in some embodiments, are particularly useful for recovering minor amounts of unreacted aromatic feed material and reaction products of solvent monocarboxylic acid from oxidation that may remain in the exhaust gas. In embodiments of the invention in which condensation of high pressure gas from separation includes one or more condensations at a temperature low enough that water in the gas is substantially, and preferably at least about 80%, condensed and volatile impurities such as lower alcohol and ester reaction products of the solvent monocarboxylic acid are substantially retained in an uncondensed exhaust gas phase that is cooled sufficiently, preferably to a temperature in the range of about 40 to about 90° C., treatment for recovery of such impurities is facilitated because the uncondensed exhaust gas from condensation is cool enough for use of liquid scrubbing agents for recovery. In other embodiments, treatment is beneficial to reduce or eliminate organic species such as such unreacted feed material and solvent by-products if not removed otherwise, as well as corrosive alkyl bromide reaction by-products from liquid phase oxidations in which a source of bromine is used as promoter for the liquid phase oxidation catalyst and carried over into the high pressure vapor phase generated in the liquid phase oxidation and, in turn, into the high pressure gas removed from separation and exhaust gas removed from condensation. It will be appreciated that such treatments can affect the amount of energy recoverable from the exhaust gas after condensation. Accordingly, in embodiments of the invention in which condensing zone exhaust gas is treated before recovery of energy in the form of work, preferred treatments are conducted without substantial loss of pressure or volume of the gas. When condensing zone exhaust gas has appreciable water content it also is preferred that any such treatment be conducted without appreciable condensation of water from the gas or cooling to such an extent that recovery of energy in the form of work results in significant condensation of water. In such embodiments, pre-heating of the treated gas before recovery of energy may be beneficial.

In embodiments of the invention comprising treating a pressurized exhaust gas from condensation for removal of unreacted feed material and solvent by-products generated in the liquid phase oxidation, such as lower alkyl esters of the solvent monocarboxylic acid, treatment is beneficial in allowing for return of such components to oxidation. Treatment also can reduce presence of such impurities in process recycle streams and steady state equilibrium levels thereof in overall process operation. Uncondensed gas under pressure removed from condensation can be contacted, preferably at a temperature of about 35 to about 60° C., with liquid scrubbing agent to provide a scrubbed gaseous phase with reduced levels of aromatic feed material, solvent or solvent by-products and a liquid product comprising the scrubbing agent and enriched in at least one of unreacted aromatic feed material, solvent monocarboxylic acid or its reaction products from liquid phase oxidation such as its corresponding alcohols and esters thereof with the solvent. The liquid product is preferably returned to the reaction zone in a liquid phase oxidation step. Scrubbing can be accomplished using any suitable scrubbing device and scrubbing agents for contacting a gas stream comprising the high pressure condensation exhaust gas to remove volatile components such as unreacted feed material, solvent monocarboxylic acid and/or its by-products from oxidation from the gas into a liquid phase. High pressure absorption columns with internal structure, such as trays or packed beds, for promoting contact between gases to be scrubbed and liquid scrubbing agent are commonly utilized. Suitable scrubbing agents are materials that are liquid at the temperature of the gas to be scrubbed and in which the materials to be recovered have substantial solubility. Examples include lower alcohols and $C_{1-8}$ carboxylic acids such as acetic acid, propionic acid, butyric acid and the like. A preferred liquid scrubbing agent is the monocarboxylic acid used as solvent for liquid phase oxidation and mixtures thereof with water. Suitable scrubbing agents, equipment and use thereof for recovery of off-gas components from liquid phase oxidation of aromatic feed materials to aromatic carboxylic acids are described in further detail in U.S. Pat. No. 6,143,925, which is incorporated herein by reference.

Pressurized condenser exhaust gas, with or without prior treatment as for scrubbing of unreacted feed material or solvent by-products as described above, can also be treated to remove corrosive or other combustible materials. While any means for such removal without substantial loss of pressure and volume of the gas can be employed, the gas preferably is subjected to an oxidation process, and most preferably a catalytic oxidation process for removal of organic, combustible and corrosive components. Such treatments generally comprise heating an uncondensed gas under pressure, and comprising exhaust gas under pressure removed from condensation or after scrubbing or other treatment, and gaseous oxygen in a combustion zone under pressure not substantially less than that of the pressurized gas and at elevated temperature effective to oxidize organic, combustible and corrosive components to a less corrosive or more environmentally compatible gas comprising carbon dioxide and water. Heating under pressure with oxygen gas preferably is conducted in the presence of a suitable oxidation catalyst disposed within the combustion zone so as not to interrupt flow of the pressurized gas therethrough. The pressurized gas can optionally be subjected to preheating before oxidation. Preheating can be accomplished by any suitable means such as by heat exchange, direct steam injection or other suitable means. Optionally, combustion treatment can also include scrubbing a pressurized gas removed from combustion to remove acidic, inorganic materials such as bromine and hydrogen bromide which are generated by oxidation of alkyl bromides present in the condenser exhaust gas when a bromine source is used for liquid phase oxidation as noted above.

Catalysts for catalytic oxidation generally comprise at least one transition group element of the Periodic Table (IUPAC). Group VIII metals are preferred, with platinum, palladium and combinations thereof and with one or more additional or adjuvant metals being especially preferred. Such catalyst metals may be used in composite forms such as oxides. Typically, the catalyst metals are disposed on a support or carrier material of lower or no catalytic activity but with sufficient strength and stability to withstand the high temperature and pressure oxidizing environment of the combustion zone. Suitable catalyst support materials include metal oxides comprising one or more metals, examples of which include mullite, spinels, sand, silica, alumina silica alumina, titania, zirconia. Various crystalline forms of such materials can be utilized, such as alpha, gamma, delta and eta aluminas, rutile and anatase titanias. Catalyst metal loadings on support compositions are suitably fractions to several percents by weight, with higher loadings being preferred for use when treating gases with significant water vapor content, such as about 20 vol. % or more. Catalysts can be used in any convenient configuration, shape or size. For example, the catalyst can be in the form of pellets, granules, rings, spheres, and the like and preferably may be formed into or disposed on a rigid cellular, honeycomb, perforated or porous structural configuration to promote contact with gases present in the combustion zone without impeding gas flow through the zone. Specific examples of catalytic oxidation catalysts for combustion treatment of exhaust gas removed from condensation in off-gas treatment according to the invention comprise about one-half to about one wt % palladium supported on an alumina monolith support.

In embodiments of the invention in which energy in the form of work is recovered from gas comprising exhaust gas removed from a condensing zone, and especially when such a gas comprises appreciable water, e.g., at least about 5 vol. %, the gas can optionally be heated to guard against presence of liquid water in the gas directed to energy recovery. Such heating can take place before, after or in combination with other treatments or treatment steps such as thermal or catalytic oxidations. In such embodiments, heating can be accomplished by any suitable technique, such as by heat exchange or direct injection of steam or other heated gas. Heating to about 200° C. or greater is effective for avoiding condensation of water, with temperatures of about 250 to about 350° C. preferred.

In addition to the condensing zone exhaust gas remaining after condensation of high pressure gas removed from the separation zone, condensation according to an off-gas treatment step of the invented process results in condensation of a liquid from the pressurized gas. The condensate liquid comprises water of substantial purity. In addition to water, the condensate contains organic impurities comprising minor amounts of solvent monocarboxylic acid and traces of low molecular weight alcohol reaction products of the solvent monocarboxylic acid, solvent monocarboxylic acid esters thereof and partial or intermediate oxidation by-products of the aromatic feed material. Water and impurities contents of the condensate can vary somewhat depending on choice and compositions of recycle streams in various embodiments of the invented process. Generally, however, water content of the condensate liquid is at least about 94 wt % and preferably 96 to about 98 wt %. Solvent monocarboxylic acid content of the liquid condensate is about 5 wt % or less, and preferably not more than about ½ to about 3 wt %. Impurities such as lower aliphatic alcohols and their esters of the solvent monocarboxylic acid formed as or from oxidation reaction products of the solvent monocarboxylic acid and oxidation by-products of the aromatic feed material typically are present at levels up to about 1 wt % each, and preferably not greater than about 500 ppmw.

The high water and low organic impurities levels of the liquid condensate make the liquid suitable, even without need for additional purification or other treatment to reduce impurities levels, for other uses, including not only wash liquids for solid-liquid separations and reflux or wash liquids in separation of water and solvent monocarboxylic acid in a high pressure vapor phase from liquid phase oxidation, but also as liquid comprising water in processes for making purified aromatic carboxylic acids. Surprisingly, the liquid condensate is suitable, even in commercial scale processes and without additional treatment or purification, not only as a crystallization solvent or wash liquids for recoveries and separations of pure forms of aromatic carboxylic acid product, but even as solvent for purification reaction solutions comprising aromatic carboxylic acid and impurities dissolved in a liquid comprising water. Accordingly, in preferred embodiments of the invented process, liquid condensate condensed from pressurized condenser exhaust gas and comprising water and substantially free of organic impurities is directed to an aromatic carboxylic acid purification process or step and used as fresh or makeup solvent for dissolving crude or impure aromatic carboxylic acid product to be purified. In such embodiments, the invented process not only reduces, or can even eliminate, requirements for demineralized or other high purity sources of water used in known aromatic carboxylic acid purification processes, but also reduces volumes of process effluent liquids that otherwise would be treated or disposed of as liquid waste.

In embodiments of the invention comprising purification or manufacture of purified aromatic carboxylic acids, at least one purification step comprises contacting with hydrogen at elevated temperature and pressure in the presence of a catalyst comprising a hydrogenation catalyst metal a purification reaction solution comprising a liquid that comprises water and has dissolved therein aromatic carboxylic acid and impurities to form a purification liquid reaction mixture comprising the aromatic carboxylic acid and hydrogenated impurities dissolved in a liquid comprising water. In preferred embodiments, a purification reaction solution is formed by dissolving in a liquid comprising water a crude solid product recovered from liquid phase oxidation comprising aromatic carboxylic acid and impurities comprising oxidation by-products of the aromatic feed material for the oxidation. Pure forms of aromatic carboxylic acid product containing reduced levels of impurities can be recovered from the purification liquid reaction mixture, preferably by crystallization, and the resulting pure form of product can be separated from a liquid purification mother liquor remaining after recovery of the pure form of product and/or from one or more liquids comprising water, such as crystallization solvents and wash liquids. At least one liquid comprising water that is used in the purification comprises condensate liquid comprising water substantially free of organic impurities recovered from a condensing zone in the off-gas treatment as described herein. According to another preferred embodiment of the invention, purification mother liquor from at least one purification is directed to off-gas treatment where it is used as reflux or wash liquid to a separation zone for substantial separation of solvent monocarboxylic acid and water vapors in a high pressure vapor phase removed from liquid phase oxidation.

As indicated above, aromatic carboxylic acid products obtained by liquid phase oxidation of feed materials comprising aromatic compounds with oxidizable substituents, also sometimes referred to as a crude aromatic carboxylic acid product or crude product from liquid phase oxidation, comprise aromatic carboxylic acid and one or more oxidation intermediates or by-products. Although specific chemical compositions of intermediates and by-products vary depending composition of the oxidation feed material, oxidation reaction conditions and other factors, and even for given feed materials may not be fully known, they are known to comprise one or more aromatic carbonyl compounds, such as benzaldehydes, carboxybenzaldehydes, fluorenones and anthraquinones, that cause or correlate with undesirable color of desired aromatic carboxylic acid products or of polyesters made therefrom and can be hydrogenated to species more soluble in aqueous solution than the aromatic carbonyl compounds and aromatic carboxylic acid or to species with less color or color-forming tendencies. Preferred impure aromatic carboxylic acid products to be purified according to the invention are crude product comprising aromatic carboxylic acid and by-products produced by liquid phase oxidation of aromatic feed material in a liquid phase oxidation, and most preferably continuous processes in which liquid phase oxidation and purification steps are integrated such that a crude solid product of liquid phase oxidation is a starting material for purification. However, it also will be appreciated that the starting material for purification can be or include an impure product comprising an aromatic carboxylic acid and aromatic carbonyl impurities as described above, whether present or generated as by-products from an integrated or non-integrated liquid phase oxidation of aromatic feed material or from other processes or sources. Thus, the invention includes embodiments in which an impure aromatic carboxylic acid product starting material for purification comprises aromatic carboxylic acid and at least one aromatic carbonyl impurity that forms a hydrogenated, carbonyl-substituted aromatic product with greater solubility in aqueous solution or less color or color-forming tendencies than the unhydrogenated aromatic carbonyl impurity.

Minor amounts of solvent monocarboxylic acid, such as residual solvent remaining in crude product from a liquid phase oxidation step also may be present in the impure aromatic carboxylic acid product subjected to purification. Amounts ranging from several hundred to thousands ppmw as commonly present in products from commercial scale liquid phase oxidations do not adversely affect purification according to the invented process. Most preferably, solvent monocarboxylic acid content of an aromatic carboxylic acid product to be purified does not exceed about 10 wt %.

In greater detail, a preferred purification step according to the invention comprises dissolving in a liquid comprising water, at least a portion of which most preferably comprises condensate liquid condensed from off-gas treatment as described herein and comprising water substantially free of organic impurities, a solid product comprising aromatic carboxylic acid and impurities to form a purification reaction solution, contacting the purification solution at elevated temperature and pressure with hydrogen in the presence of a hydrogenation catalyst to form a purification liquid reaction mixture, recovering from the purification liquid reaction mixture a solid purified product comprising aromatic carboxylic acid with reduced levels of impurities and separating an aqueous liquid purification mother liquor comprising oxidation by-products, hydrogenation products thereof and combinations thereof from the recovered solid purified product.

Hydrogenation of impure aromatic carboxylic acids to reduce impurities levels is conducted with the impure acid in aqueous solution. Condensate liquid condensed from the pressurized exhaust gas condensed from high pressure gas from separation in at least one off-gas treatment step as described herein is a preferred solvent for the purification solution. Supply of condensate liquid directly from condensation and without added or intermediate treatments for removal of by-products or other impurities is preferred in continuous and integrated process operations to avoid costs, complexities and additional equipment for added handling, storage or treatment of the condensate liquid, although it will be appreciated that such added treatments, while unnecessary to render the condensate liquid suitable as a solvent for purification, are not precluded. Similarly, while unnecessary for obtaining a liquid of sufficient purity for use as purification solvent according the invention, it will be appreciated that the invention contemplates use of liquid condensate from condensation in combination with fresh demineralized water or other purified sources of water. Preferably liquid condensate recovered from condensation of a high pressure gas from separation according to the invention makes up at least about 50% of the solvent for the purification reaction solution and more preferably about 80 to about 100%.

Concentrations in the purification solvent of impure aromatic carboxylic acid to be treated in a purification step generally are low enough that the impure acid is substantially dissolved and high enough for practical process operations and efficient use and handling of liquid used as solvent and remaining as purification mother liquor after recovery of a pure form of aromatic carboxylic acid with reduced impurities from purification reaction mixtures. Suitably, solutions comprising about 5 to about 50 parts by weight impure aromatic carboxylic acid per hundred parts by weight solution at process temperatures provide adequate solubility for practical operations. Preferred purification reaction solutions contain about 10 to about 40 wt %, and more preferably about 20 to about 35 wt %, impure aromatic carboxylic acid at the temperatures used for purification by catalytic hydrogenation.

Catalysts suitable for use in purification hydrogenation reactions comprise one or more metals having catalytic activity for hydrogenation of impurities in impure aromatic carboxylic acid products, such as oxidation intermediates and by-products and/or aromatic carbonyl species. The catalyst metal preferably is supported or carried on a support material that is insoluble in water and unreactive with aromatic carboxylic acids under purification process conditions. Suitable catalyst metals are the Group VIII metals of the Periodic Table of Elements (IUPAC version), including palladium, platinum, rhodium, osmium, ruthenium, iridium, and combinations thereof. Palladium or combinations of such metals that include palladium are most preferred. Carbons and charcoals with surface areas of several hundreds or thousands $m^2/g$ surface area and sufficient strength and attrition resistance for prolonged use under operating conditions are preferred supports. Metal loadings are not critical but practically preferred loadings are about 0.1 wt % to about 5 wt % based on total weight of the support and catalyst metal or metals. Preferred catalysts for conversion of impurities present in impure aromatic carboxylic acid products comprising crude terephthalic acid obtained by liquid phase oxidation of a feed material comprising para-xylene contain about 0.1 to about 3 wt % and more preferably about 0.2 to about 1 wt % hydrogenation metal. For such uses, the metal most preferably comprises palladium.

For practical applications, catalyst is most preferably used in particulate form, for example as pellets, extrudate, spheres or granules, although other solid forms also are suitable. Particle size of the catalyst is selected such that a bed of catalyst particles is easily maintained in a suitable purification reactor but permits flow of the purification reaction mixture through the bed without undesirable pressure drop. Preferred average particle sizes are such that catalyst particles pass through a 2-mesh screen but are retained on a 24-mesh screen (U.S. Sieve Series) and, more preferably, through a 4-mesh screen but with retention on a 12-mesh and, most preferably 8-mesh, screen.

Contacting aqueous purification reaction solution with hydrogen in the presence of catalyst for purification is conducted at elevated temperatures and pressures. Temperatures range from about 200 to about 370° C., with about 225 to about 325° C. being preferred and about 240 to about 300° C. being most preferred. Pressure is at a level sufficient to maintain a liquid phase comprising the aqueous reaction solution. Total pressure is at least equal to, and preferably exceeds, the sum of the partial pressures of the hydrogen gas introduced to the process and water vapor that boils off from the aqueous reaction solution at the temperature of operation. Preferred pressures are about 35, and more preferably about 70, to about 105 $kg/cm^2$.

The aqueous purification reaction solution is contacted with hydrogen gas under hydrogenation conditions as described above in a suitable reaction vessel capable of withstanding reaction temperatures and pressures and also the acidic nature of its liquid contents. A preferred reactor configuration is a cylindrical reactor with a substantially central axis which, when the reactor is positioned for process use, is vertically disposed. Both upflow and downflow reactors can be used. Catalyst typically is present in the reactor in one or more fixed beds of particles maintained with a mechanical support for holding the catalyst particles in the bed while allowing relatively free passage of reaction solution therethrough. A single catalyst bed is often preferred although multiple beds of the same or different catalyst or a single bed layered with different catalysts, for example, with respect to particle size, hydrogenation catalyst metals or metal loadings, or with catalyst and other materials such as abrasives to protect the catalyst, also can be used and may provide benefits. Mechanical supports in the form of flat mesh screens or a grid formed from appropriately spaced parallel wires are commonly employed. Other suitable catalyst retaining means include, for example, a tubular Johnson screen or a perforated plate. Internal components and surfaces of the reactor and the mechanical support for the catalyst bed are constructed of materials that are suitably resistant to corrosion from contact with the acidic reaction solution and reaction product mixture. Most suitably, supports for catalyst beds have openings of about 1 mm or less and are constructed of metals such as stainless steel, titanium or Hastelloy C.

In preferred embodiments of the invention, aqueous solution of impure aromatic carboxylic acid to be purified is added to the reactor vessel at elevated temperature and pressure at a position at or near the top portion of the reactor vessel and the solution flows downwardly through the catalyst bed contained in the reactor vessel in the presence of hydrogen gas, wherein impurities are reduced with hydrogen, in many cases to hydrogenated products with greater solubility in the reaction mixture than the desired aromatic carboxylic acid or with less color or color-forming tendencies. In such a preferred mode, a liquid purification reaction mixture comprising aromatic carboxylic acid and hydrogenated impurities is removed from the reactor vessel at a position at or near a lower portion or bottom of the reactor.

Reactors used for purification may be operated in several modes. In one mode, a predetermined liquid level is maintained in the reactor and, for a given reactor pressure, hydrogen is fed at a rate sufficient to maintain the predetermined liquid level. The difference between the actual reactor pressure and the vapor pressure of the vaporized purification solution present in the reactor head space is the hydrogen partial pressure in the head space. Alternatively, hydrogen can be fed mixed with inert gas such as nitrogen or water vapor, in which case the difference between the actual reactor pressure and the vapor pressure of the vaporized reaction solution present is the combined partial pressure of hydrogen and the inert gas mixed therewith. In such cases hydrogen partial pressure may be calculated from the known relative amounts of hydrogen and inert gas present in the mixture.

In another operating mode, the reactor can be filled with the aqueous liquid reaction solution so that there is essentially no reactor vapor space but a hydrogen bubble at the top or in the head of the reactor that expands or contracts in size to provide volume in the reactor head so that hydrogen added to the reactor is dissolved into the incoming purification reaction solution. In such an embodiment, the reactor is operated as a hydraulically full system with dissolved hydrogen being fed to the reactor by flow control. The concentration of hydrogen in solution may be modulated by adjusting the hydrogen flow rate to the reactor. If desired, a pseudo-hydrogen partial pressure value may be calculated from the solution hydrogen concentration which, in turn, may be correlated with the hydrogen flow rate to the reactor.

When operating such that process control is effected by adjusting the hydrogen partial pressure, the hydrogen partial pressure in the reactor is preferably in the range of about one-half to about 15 $kg/cm^2$ gauge or higher, depending on pressure rating of the reactor, impurities levels of the impure aromatic carboxylic acid, activity and age of the catalyst and other considerations known to persons skilled in the art. In operating modes involving directly adjusting hydrogen concentration in the feed solution, the solution usually is less than saturated with respect to hydrogen and the reactor itself is hydraulically full. Thus, an adjustment of the hydrogen flow rate to the reactor will result in the desired control of hydrogen concentration in the solution.

Space velocity, expressed as weight of the impure aromatic acid in the purification reaction solution per weight of catalyst per hour, during hydrogenation is typically about 1 $hour^{-1}$ to about 25 $hour^{-1}$, and preferably about 2 $hours^{-1}$ to about 15 $hours^{-1}$. Residence time of the purification liquid stream in the catalyst bed varies depending on the space velocity.

Pure forms of aromatic carboxylic acid product with reduced levels of impurities relative to the crude or other impure aromatic carboxylic acid product used for preparing the purification solution is recovered from the liquid purification reaction mixture. The purification reaction mixture, comprising aqueous reaction solvent having dissolved therein aromatic carboxylic acid and hydrogenated aromatic impurities having greater solubility in the aqueous reaction liquid than their unhydrogenated precursors, is cooled to separate a pure form of solid aromatic carboxylic acid with reduced impurities from the reaction mixture, leaving a liquid purification mother liquor having hydrogenated impurities dissolved therein. Separation is commonly achieved by cooling to a crystallization temperature, which is sufficiently low for crystallization of the aromatic carboxylic acid to occur, thereby producing crystals within the liquid phase. The crystallization temperature is sufficiently high so that dissolved impurities and their reduction products resulting from hydrogenation remain dissolved in the liquid phase. Crystallization temperatures generally range up to 160° C. and preferably up to about 150° C. In continuous operations, separation normally comprises removing liquid purification reaction mixture from the purification reactor and crystallization of aromatic carboxylic acid in one or more crystallization vessels. When conducted in a series of stages or separate crystallization vessels, temperatures in the different stages or vessels can be the same or different and preferably decrease from each stage or vessel to the next. Crystallization typically also results in flashing of liquid from the purification liquid reaction mixture, which can be recovered by condensation and recycled to one or more of purification, one or more upstream crystallization stages or, in preferred embodiments of the invention, to separation of solvent monocarboxylic acid and water vapor in a high pressure vapor phase from liquid phase oxidation. Liquid comprising water, which preferably comprises condensate liquid comprising water substantially free of organic impurities recovered from a high pressure gas from separation of solvent monocarboxylic acid and water vapors in a high pressure vapor phase from liquid phase oxidation, is preferably added to the crystallized product recovered from purification liquid reaction mixture recovered in stagewise crystallizations either directly or, more preferably, indirectly in one or more wash liquids for the crystallized product.

Thereafter, crystallized, purified aromatic carboxylic acid product is separated from the purification mother liquor, including hydrogenated impurities dissolved therein. Separation of the crystallized product is commonly conducted by centrifuging or by filtration. A preferred separation comprises pressure filtration of an aqueous slurry of pure forms of aromatic carboxylic acid and washing of filter cake resulting from filtration with a liquid comprising water as described in U.S. Pat. No. 5,175,355, which is incorporated herein by reference. Condensate liquid condensed from off-gas treatment as described herein is a preferred liquid comprising water for use as wash liquid for the pure form of aromatic carboxylic acid.

Purification mother liquor remaining after recovery of solid purified aromatic carboxylic acid from the purification reaction mixture comprises water and hydrogenated derivatives of by-products or impurities present in the impure aromatic carboxylic acid starting material. The mother liquor commonly also includes minor amounts of aromatic carboxylic acid that remain in solution. Such hydrogenated derivatives include compounds suitable for conversion to aromatic carboxylic acid by liquid phase oxidation and, accordingly, in preferred embodiments of the invention, at least a portion of such hydrogenated derivatives are transferred directly or indirectly to a liquid phase oxidation. Residual aromatic carboxylic acid present in the mother liquor also can be transferred directly or indirectly to liquid phase oxidation after separation from, or more preferably, together with, such hydrogenated derivatives. Transfer of such derivatives and aromatic carboxylic acid to oxidation is conveniently accomplished by directing at least a portion of a purification mother liquor remaining after separation of a solid pure form of aromatic carboxylic acid to a liquid phase oxidation step. Water content of purification mother liquor can upset water balance in oxidation unless water from purification mother liquor directed to oxidation is accounted for in other streams that may be returned to oxidation. Transfer of hydrogenated impurities in a purification mother liquor, alone or preferably in combination with aromatic carboxylic acid present in the mother liquor, to liquid phase oxidation is preferably accomplished without upsetting water balance in the oxidation. More preferably, at least a portion, and most preferably substantially all, of a liquid mother liquor remaining after separation of the solid purified aromatic carboxylic acid from the liquid purification reaction mixture is transferred directly or indirectly to a separation zone of off-gas treatment of a high pressure vapor phase removed from oxidation according to the invention where it is used as reflux liquid. For example, if one or more distillation columns are used for separation of solvent monocarboxylic acid and water in a high pressure vapor phase generated by liquid phase oxidation of aromatic feed material, purification mother liquor can be used in whole or in part as reflux for one or more columns. Water present in mother liquor added as reflux is substantially vaporized, entering the vapor phase in the tower, with water retained in the vapor phase that exits the tower becoming part of the pressurized gas from separation. Higher boiling components of the mother liquor, including hydrogenated impurities such as liquid phase oxidation by-products of the aromatic feed material for the oxidation and aromatic carboxylic acid if present, remain substantially in the liquid phase and can be returned directly or indirectly to a liquid phase oxidation reaction mixture, for example as part of the solvent monocarboxylic acid-rich liquid phase resulting from separation or in a stream separately removed from separation.

Purification reactor and catalyst bed configurations and operating details and crystallization and product recovery techniques and equipment useful in the process according to this invention are described in further detail in U.S. Pat. No. 3,584,039, U.S. Pat. No. 4,626,598, U.S. Pat. No. 4,629,715, U.S. Pat. No. 4,782,181 U.S. Pat. No. 4,892,972, U.S. Pat. No. 5,175,355, U.S. Pat. No. 5,354,898, U.S. Pat. No. 5,362,908 and U.S. Pat. No. 5,616,792 which are incorporated herein by reference.

FIG. 1 illustrates in further detail an apparatus according to the invention and for operation of processes for manufacture of aromatic carboxylic acids according to the invention. The apparatus comprises a reaction vessel having a vent for removing reactor overhead vapor; a separation device capable of substantially separating $C_{1-8}$ monocarboxylic acid and water vapors in a gaseous mixture under pressure comprising the monocarboxylic acid and water, the separation device being in fluid communication with the reaction vessel so as to receive a high pressure vapor phase removed from the vent in the reaction vessel; condensing means in fluid communication with the separation device adapted to extract energy from a high pressure gas by condensing at least a portion of the high pressure gas and exchanging heat with a heat sink material; and means for directing liquid condensate condensed from the high pressure gas from the condensing means to at least one vessel of an aromatic carboxylic acid purification apparatus. The figure also depicts a preferred embodiment in which the apparatus also includes an expander in fluid communication with the condensing means for recovering energy from an exhaust gas under pressure removed from the condensing means.

A preferred form of apparatus, also represented in the figure, comprises a pressure rated reaction vessel that defines a substantially enclosed interior volume adapted to containing a liquid reaction mixture and an overhead vapor and comprising at least one inlet for introducing a liquid to the interior volume, at least one inlet for introducing a gas comprising oxygen and under pressure to the interior volume, at least one liquid product outlet for removing from the interior volume a product comprising a liquid or slurry of solid in a liquid, and at least one vent for removing a high pressure off-gas from the interior volume; a separation device in fluid communication with the reaction vessel for receiving into the device a high pressure off-gas removed from at least one vent in the reaction vessel and comprising at least column comprising at least one vapor inlet adapted to receive a high pressure off-gas into the column into a high pressure vapor phase flow therethrough, at least one liquid inlet adapted to receive reflux liquid into a refluxing liquid flow through the column countercurrent to the high pressure vapor flow, means within the column and positioned intermediate vapor and liquid inlets and providing surface for contacting vapor and liquid phases within the column such that a high pressure vapor phase comprising gaseous $C_{1-8}$ monocarboxylic acid and water vapor received into the column is separated into a liquid phase rich in the $C_{1-8}$ monocarboxylic acid but lean in water and a high pressure gas comprising water and not more than about 10% of the $C_{1-8}$ monocarboxylic acid in the high pressure off-gas received into the column, at least one liquid outlet for removing a liquid therefrom, and at least one vent located above the liquid inlet for removal from the column of the high pressure gas comprising water; at least one condensing means in fluid communication with the separation device for receiving a high pressure gas comprising water comprising at least one gas inlet adapted to receive the high pressure gas comprising water, at least one vent adapted for removal of a high pressure exhaust gas from the condensing means, heat transfer means for exchanging heat between a high pressure gas introduced to the condensing means and a heat transfer medium and condense from the gas a liquid comprising water; and means for directing liquid comprising water recovered in the condensing means to one or more liquid receptacles in an apparatus for purifying aromatic carboxylic acid Referring to FIG. 1, oxidation reaction vessel 10 comprises a substantially cylindrical shell that defines a substantially enclosed interior volume. In use, a lower portion of the interior volume contains a liquid reaction body while an overhead reaction off-gas is contained in a portion of the interior volume above the liquid level. The interior volume is in communication with the exterior of the reaction vessel through a plurality of inlets, such as represented as at 12a, b, c and d, through which liquid aromatic feed material, solvent and soluble forms of catalyst are introduced from liquid charge vessels (not shown) and compressed air or another source of oxygen gas is introduced from a compressor or other suitable device (not shown) via suitable transfer lines (as at 13 which is in flow communication with inlet 12a). The inlets preferably are disposed such that liquid and gaseous components are introduced below the liquid level in the interior of the vessel. The reaction vessel also includes at least one outlet, as at 14, for removing from the interior a liquid phase reaction mixture which includes a crude product comprising aromatic carboxylic acid and oxidation by-products, the same typically being present in solution in the liquid or as solid particles suspended or slurried in the liquid or both dissolved and suspended in the liquid. Reaction vessel 10 also comprises at least one vent or outlet 16 for removal from the vessel interior of a high pressure vapor phase evaporated from the liquid reaction body. Vent 16 preferably is positioned to correspond to an upper portion of the vessel when it is in position for process use.

A preferred reaction vessel design is a substantially cylindrical vessel having a central axis extending substantially vertically when the vessel is positioned for process use. The vessel is adapted for use with a stirring mechanism, such as represented at 18 with shaft 20 having one or more impellers 22 and 24 mounted thereon and capable of being rotated within the interior of the reaction vessel to stir the liquid reaction mixture present in the vessel during process use. In preferred embodiments of the invention, at least two impellers or mixing features are mounted on the shaft for mixing of gaseous and liquid components within the liquid reaction body without adverse settling of solids in lower portions of the vessel. Axial flow impellers, generally configured as propellers, radial flow mixers, such as flat blade disc turbines and disperser discs, helical ribbon mixing elements, pitched blade turbines with blades pitches for upward or downward flow, anchor-type mixers providing predominantly tangential flow and other configurations are suited for mixing the liquid phase oxidation reaction system and preferably are used in various combinations to account for greater solids content in lower regions of the liquid reaction mixture, greater gas content in upper regions and other characteristics of the liquid phase reaction mixture that can vary throughout the liquid body. Other designs are disclosed in U.S. Pat. No. 5,198,156, describing mixing elements with radially extending, rotating blades mounted on a flat rotor and having a hollow blade configuration with a discontinuous leading edge, continuous trailing edge, absence of external concave surfaces and an open outer end and preferably used in conjunction with a vertical pipe or perforated gas sparger for gas distribution, and U.S. Pat. No. 5,904,423, which describes a mixer in which stirring elements are mounted at a downward angle on a central, rotating shaft and are wedge-shaped in the direction of movement through the liquid, with radial inner ends of the trailing edges of the blades angled outwardly in the direction of motion of the blades, and used with features for introducing a gas from below the stirring elements into a central cavity formed by a conical disk at an end of the shaft.

At least those portions of the reaction vessel, agitator shaft and mixing elements that contact the liquid reaction mixture and overhead gas in process use are constructed of substantially corrosion resistant materials. Examples include titanium metal and alloys and duplex stainless steels. Titanium metal is preferred.

The reaction vessel is in flow communication with a separation device such that a high pressure overhead gas removed from the vessel through at least one overhead gas vent, as at 16, is received into the separation device.

The separation device is designed so that in operation it is capable of substantially separating $C_{1-8}$ monocarboxylic acid vapor from water vapor in a high pressure reactor overhead gas introduced to the device such that a liquid phase rich in the monocarboxylic acid and a high pressure separation overhead gas substantially free of the acid but rich in water vapor are formed. A pressure rated column or tower, or a series of columns or towers, equipped with at least one inlet for receiving a high pressure gas, at least one inlet for introduction of reflux liquid, at least one outlet for removing a high pressure gas from the separation, and a fractionating zone comprising internal structure providing surface to promote mass transfer between countercurrently flowing gas and liquid phases sufficient to provide suitable theoretical equilibrium stages for separation of solvent monocarboxylic acid and water in the vapor phase is a preferred separation device. Preferably, the device is designed for introduction of an inlet gas into a lower portion of the column or tower and introduction of reflux liquid at one or more upper location relative to the gas inlet and with an intermediately positioned fractionating zone so that countercurrent flow therethrough results from upward passage of vapor phase and downward flow, under force of gravity, of liquid supplied as reflux and condensed from the ascending vapor phase. Additional features of such a tower or column can comprise one or more outlet or inlet ports for removal or addition of one or more gas or liquid streams, for example, removal of a liquid rich in monocarboxylic acid separated from the vapor phase.

The separation device can also be provided with a reboiler or other suitable means for supplemental heat input although such means are not normally needed when a high pressure vapor phase from a liquid phase oxidation reaction vessel is introduced substantially directly to the device or otherwise without appreciable cooling because the oxidation reactor effectively serves as a reboiler by reason of the exothermic nature of the oxidation reaction. In preferred embodiments, direct association or close coupling of the oxidation reactor and separation device are effectuated by connection directly or by suitable pressure rated piping or other conduits between one or more vents in the oxidation reaction vessel and one or more gas inlets to a separation device, such that a vapor phase under liquid phase reaction conditions is removed from the reaction vessel and introduced into the separation device at the same or substantially the same temperature and pressure as in the reaction zone.

Preferably, the separation device is capable of separating water and solvent monocarboxylic acid vapors in the high pressure gas introduced to the device such that a liquid phase with at least about 60 to 85 parts by weight solvent monocarboxylic acid per hundred parts by weight of the liquid and a high pressure gas containing about 45 to 65 parts by weight water per hundred parts by weight of the gas are formed. To achieve such separation, the fractionating zone of the separation device is configured with a plurality of theoretical equilibrium stages such as can be provided by internal trays, structured packing, combinations of trays and packing beds, or other structure or combinations thereof providing surfaces within the interior of the device for mass transfer between gaseous and liquid phases present in the device. At least about 20 theoretical equilibrium stages are preferred for such separations. Separation efficiency increases with increasing theoretical equilibrium stages, other things being equal, so there is no theoretical upper limit to the number of equilibrium stages that may be included in the separation devices used according to the invention. However, for practical purposes, separation such that an outlet gas from the separation device contains 10 wt. % or less of the solvent monocarboxylic acid content of the inlet vapor phase to the device can be accomplished with at least about 20 theoretical equilibrium stages and degrees of separation beyond that provided by about 70 such stages make additional stages impractical or economically inefficient.

A preferred separation device with structured packing has at least about 3 beds or zones of packing, and more preferably about 4 to about 6 such beds, to provide adequate surface and theoretical equilibrium stages for separation. An example of a suitable packing material is Flexipac structured packing, which is available from KGGP LLC in the form of thin sheets of corrugated metal arranged in a crisscrossing relationship to create flow channels and such that their intersections create mixing points for liquid and vapor phases. A preferred separation device with trays includes 30 to about 90 trays, at least about 70% of which are positioned between an inlet for the high pressure gas introduced to the separation device from the reaction vessel and a reflux liquid inlet. Trays in the form or sieve or bubble cap trays are preferred and preferably have separation efficiencies of about 30 to about 60%. The number of trays for a given number of theoretical equilibrium stages can be calculated by dividing the number of stages by efficiency of the trays In process use, gas and liquid phases introduced into the separation device and present therein are at elevated temperatures and include water, monocarboxylic acid and other corrosive components, for example, bromine compounds and their disassociation products such as hydrogen bromide that are present in an oxidation reaction overhead gas when the catalyst used for the oxidation includes a source of bromine. Therefore, in preferred embodiments of the invention, internal structure and other features of the separation device that contact gases and liquids during process operation are constructed of suitable metals to resist corrosion and other damage due to such contact. Titanium metal is a preferred material of construction for such surfaces, including trays, packings or other structure of the fractionating zone. Titanium surfaces of such structure may be subject to undesirable accumulation of solid deposits comprising iron oxides from impurities present in various process liquids circulated through the equipment. Processes for controlling accumulations of iron oxide deposits or content of soluble iron impurities in process liquids are described in commonly assigned U.S. Pat. No. 6,852,879 and US 2002/374719 which are incorporated herein by reference.

In the embodiment of the invention represented in FIG. 1, the separation device is a high pressure distillation column 30 having a gas inlet 34 for receiving off-gas removed from oxidation reactor 10 and a plurality of trays, individual examples of which are illustrated at 31, 33, 35 and 37. The distillation column comprises at least one lower outlet, as at 32, for removal of a liquid stream from the column, for example to oxidation reactor 10 through line 60, optionally by way of one or more intermediate holding tanks or reservoirs (not shown). The column also includes at least one liquid inlet, as at 36, which is disposed at an upper portion of the column relative to liquid outlet 32 and above all or most of the trays for adding reflux liquid to the tower, such as by pumping liquid from a reflux reservoir or directly from suitable vessels used in purification steps (not shown) through line 61. The column also includes at least one gas outlet 38 for removing from the column a high pressure gas from separation.

Distillation column 30 can be configured with one or more additional liquid inlets as at 44, for introduction of reflux liquid in addition to reflux liquid added as at inlet 36. Introducing reflux liquid at locations separated from each other by one or more, and preferably about 2 to about 10 theoretical equilibrium stages, can be beneficial in the case of reflux liquid streams containing certain oxidation by-products, and especially by-products of the aromatic hydrocarbon feed to liquid phase oxidation and/or hydrogenated derivatives thereof such as may be introduced in reflux liquids comprising a purification mother liquor or other recycle streams. Additional reflux supplied as at inlet 44 can serve to prevent such by-products from entering the vapor phase rising above introduction point 44, thereby diminishing their presence in the high pressure gas resulting from separation and removed from column 30.

The separation device of the apparatus according to this aspect of the invention is in flow communication with condensing means. The condensing means is adapted to receive a gas stream comprising high pressure gas removed from the separation device and to condense from the gas stream a liquid condensate comprising water substantially free of organic impurities, also leaving a high pressure condenser exhaust gas that comprises incondensable components of the gas introduced to the separation device and may also include water vapor if not substantially completely condensed from the high pressure inlet gas to the condensing means. The condensing means also comprises at least one outlet for removing condensate liquid condensed from the gas introduced thereto and uncondensed gas under pressure therefrom and indirect heat exchange means for transferring heat between the inlet gas and a heat exchange fluid that is introduced to the device at a lower temperature or pressure and removed at a higher temperature or pressure. The condensing means also includes means for directing condensate liquid to purification equipment, with such means preferably being in flow communication with at least one vessel or liquid receiving means in a purification process apparatus such that condensate liquid removed through an outlet for removal of condensate can be transferred directly to the purification equipment. The condensing means can also include means for directing condensate liquid to separation for use as reflux liquid. The condensing means can comprise a single or series of heat exchange devices, such as shell and tube heat exchangers, plate and frame heat exchangers or other suitable heat exchange devices, in which heat from the inlet gas is transferred to a heat exchange medium such as water, steam or another heat transfer fluid, to increase the temperature or pressure of the heat exchange fluid. Use of multiple heat exchange devices in series can be advantageous for generating steam or other heat exchange fluids at different pressures or temperatures, and condensate liquid at different temperatures, for usages with different steam pressure and liquid temperature requirements or preferences.

The condenser is constructed of metals or alloys characterized by corrosion resistance suited to the nature of the high temperature gas streams and cooled liquids present circulated or present therein during process use. Stainless steel internal surfaces are preferred, although other metals and alloys are also suitable.

Referring again to FIG. 1, the separation device, as represented by distillation column 30, is in fluid communication via vent 38 and associated transfer lines, as at 39, with condensing means 50. In the figure, condensing means 50 is made up of two condensers, 52 and 62 in series, each configured with suitable gas inlets, as at 54 and 64, respectively and outlets for removing gases and liquids therefrom, as at 56 and 66, respectively. Condenser effluent, including condensate liquid and uncondensed exhaust gas under pressure, is passed via conduit 67 to drum 68 for disengagement of uncondensed gas from condensate liquid. Exhaust gas is directed from drum 68 to further processing via line 69 and condensate liquid is removed to line 71 for transfer to one or more vessels for purification of aromatic carboxylic acid by hydrogenation of a purification reaction solution comprising a liquid comprising water having dissolved therein aromatic carboxylic acid and by-products of liquid phase oxidation or aromatic carbonyl impurities suitable for conversion to hydrogenated derivatives more soluble than the impurities in aqueous solution.

In the preferred embodiment of the invented apparatus depicted in FIG. 1, the apparatus also includes power recovery device, such as expander 90, for generating energy in the form of work from a gas stream under pressure comprising uncondensed pressurized exhaust gas removed from the condensing means, as from disengagement drum 68 via line 69. The power recovery device preferably is a gas expander or turbine adapted for expansion of the volume of gas introduced to the device by reducing pressure of the gas stream and translating the expansion into mechanical work such as by rotation of a turbine. The expander can be in direct communication with the condensing means, as illustrated in FIG. 1. Alternatively, the condensing means can communicate indirectly with the power recovery device such that before being introduced to the power recovery device the gas under pressure is transferred to one or more intermediate means (not shown) for treating the gas without substantial loss of pressure, such as in a high pressure scrubber or absorption tower for selective removal or recovery of traces of process chemicals or by-products remaining in the gas, or in a thermal or catalytic oxidation system or other pollution control device to remove corrosive or combustible components of the gas.

Liquid and gaseous streams and materials used and present in the process are typically directed and transferred through suitable transfer lines, conduits and piping constructed of appropriate materials for process use and safety. It will be understood that particular elements may be physically juxtaposed and can, where appropriate, have flexible regions, rigid regions or both. In directing streams or compounds, intervening apparatus or optional treatments can be included. For example, appropriate pumps, valves, manifolds, gas and liquid flow meters and distributors, sampling and sensing devices and other equipment for monitoring, controlling, adjusting and diverting pressures, flows and other operating parameters may be present.

Figure 2:
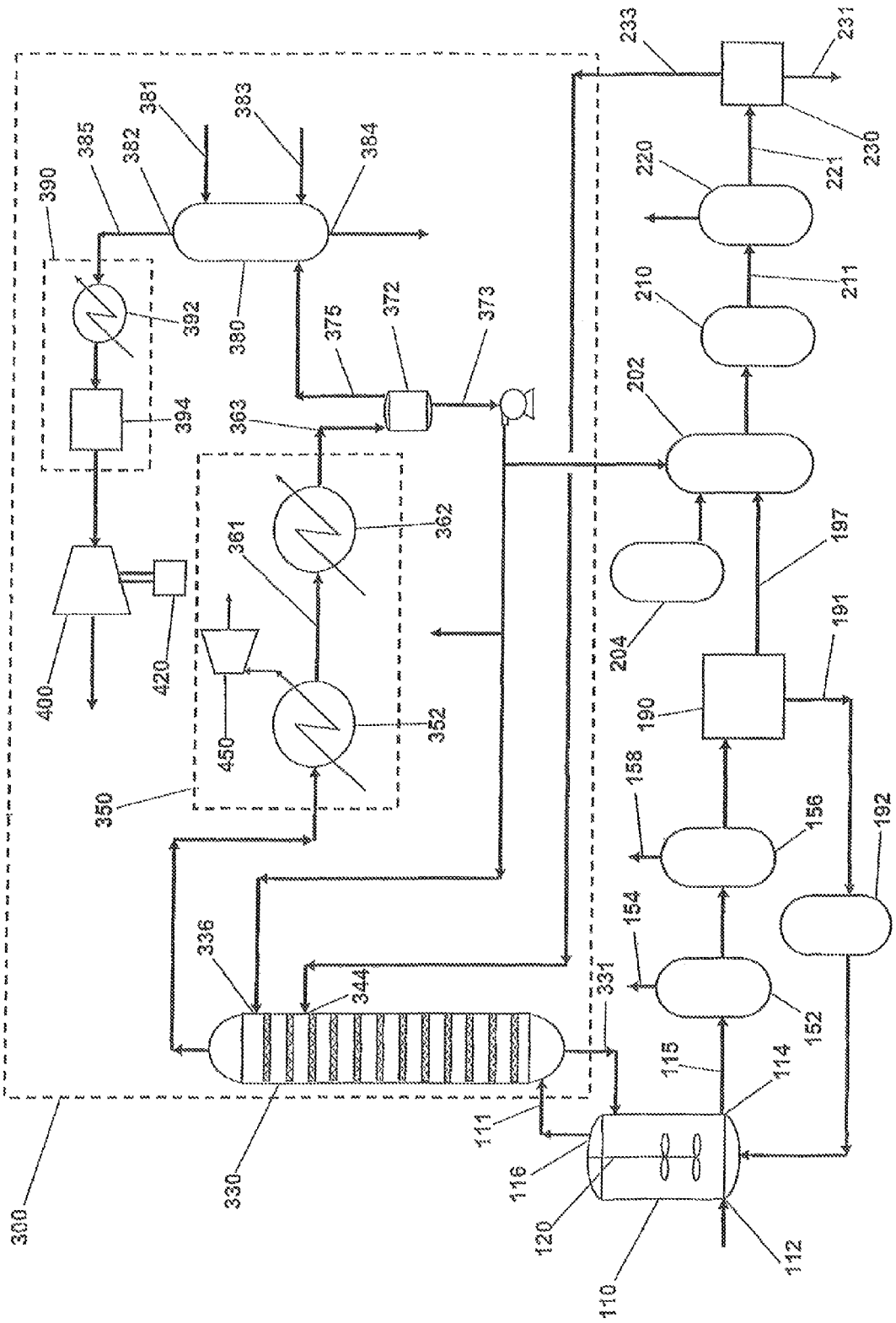
FIG. 2 is a flow diagram illustrating a process according to preferred embodiments of the invention and integration of an apparatus according to the invention, such as in FIG. 1, and equipment used for purification of aromatic carboxylic acids according to embodiments of the invention.

Aspects and embodiments of the invention are illustrated further in FIG. 2 and the following discussion thereof. While the figure is described with specific reference to manufacture of a selected aromatic carboxylic acid, terephthalic acid, by liquid phase oxidation of para-xylene as a preferred feedstock in a liquid phase reaction mixture comprising water and acetic acid as solvent monocarboxylic acid for the oxidation, off-gas treatment for separation of acetic acid and water from a high pressure vapor phase removed from oxidation and condensation of a high pressure gas removed from the separation to recover condensate liquid comprising water, and a purification step for hydrogenating a purification reaction solution comprising a crude terephthalic acid product of the liquid phase oxidation dissolved in purification reaction solvent, it will be understood that specific embodiments, features, details and preferences are described to aid in understanding the invention but not to limit the invention or its features in any aspect or embodiment.

The process illustrated in FIG. 2 also reflects preferred embodiments of the invented process in which liquid phase oxidation, off-gas treatment and purification are integrated such that crude aromatic carboxylic acid product from the liquid phase oxidation is directed to purification for use to form the purification solution, a high pressure off-gas from the oxidation is directed to the off-gas treatment, and a condensate liquid from the off-gas treatment is directed to the purification for use as solvent for the purification solution and other uses; however, it will be understood that the invention is not to be considered limited to the particular integration scheme represented in the figure and that various multiple train, shared train and other configurations are contemplated according to the invention. By way of illustrative examples, product comprising aromatic carboxylic acid and reaction by-products from multiple liquid phase oxidations can be directed to a single purification step in which liquid condensed from a high pressure gas from off-gas treatment of a high pressure vapor phase from one or more of those or other liquid phase oxidations is directed for use as a liquid comprising water. As additional such examples, crude product from a single liquid phase oxidation can be purified in separate purification trains operated in parallel, with high pressure vapor phase from the liquid oxidation subjected to off-gas treatment for recovery of condensate liquid and transfer thereof to either or both such purification trains, or as an alternative or in addition, to a process in which impure aromatic carboxylic acid from a separate oxidation or process is purified in a purification process or process steps as described herein.

Referring to FIG. 2, liquid para-xylene feed material comprising at least about 99 wt % para-xylene, aqueous acetic acid solution, preferably containing about 70 to about 95 wt % acetic acid, soluble compounds of cobalt and manganese, such as their respective acetates, as sources oxidation catalyst metals and of bromine, such as hydrogen bromide as promoter for the catalyst and air are continuously charged to oxidation reaction vessel 110, which is a pressure rated, continuous stirred tank reactor, through inlets, one of which is depicted for purposes of illustration as at 112. Solvent and para-xylene feed are charged at rates providing a solvent to feed weight ratio of abut 2:1 to about 5:1. Cobalt and manganese sources preferably are used in amounts providing about 100 to about 800 ppmw each based on weight of para-xylene feed material. Bromine preferably is used in an amount such that the atom ratio of bromine to catalyst metals is about 0.1:1 to about 1.5:1.

Stirring is provided by rotation of shaft 120 driven by an external power source (not shown) causing impellers mounted on the shaft and located within the liquid body in the reactor to provide forces for mixing of liquids and dispersion of gases within the liquid body and avoiding settling of solids in its lower regions. Catalyst and promoter, each preferably as a solution in acetic acid solvent, are introduced into the liquid body in the reaction vessel. Air is supplied from below and within the sweep path of a lower impeller at a rate effective to provide at least about 3 moles molecular oxygen per mole of aromatic feed material.

Para-xylene oxidizes in the stirred liquid reaction mixture in reactor 110, predominantly to terephthalic acid, but also reacts to form by-products including partial and intermediate oxidation products, such as 4-carboxybenzaldehyde, 1,4-hydroxymethyl benzoic acid and p-toluic acid, and others such as benzoic acid. Solid reaction products comprising terephthalic acid and para-xylene oxidation by-products precipitate from the liquid reaction mixture, with lesser amounts thereof remaining dissolved in the liquid. Solids content of the liquid slurry typically ranges up to about 40 wt. % and preferably from about 20 to about 35 wt. %. Water is also generated as a product of the oxidation. The oxidation reaction is exothermic and heat generated by the reaction causes boiling of the liquid phase reaction mixture and formation of an overhead vapor phase comprising vaporized acetic acid, water vapor, gaseous by-products of the oxidation reaction, carbon oxides, nitrogen from the air charged to the reaction and unreacted oxygen. The interior volume of reactor 110 is maintained under pressure sufficient to maintain the liquid phase nature of the reaction mixture, preferably at about 5 to about 21 kg/cm$^2$ gauge. Overhead vapor is removed from the reactor through vent 116. The reactor contents are maintained at an operating temperature in the range of about 160 to about 225° C. based on the rate of removal of the vapor phase also taking into account temperatures and flow rates of streams removed from and returned to the reactor as described below.

A liquid effluent comprising solid para-xylene oxidation products, including terephthalic acid, slurried in the liquid phase reaction mixture, which also contains dissolved para-xylene, oxidation by-products and catalyst metals, is removed from reaction vessel 110 through a slurry outlet as at 114 and directed in stream 115 to a crystallization zone for recovery of a solid product of the oxidation comprising terephthalic acid and oxidation by-products of the para-xylene feedstock.

In the embodiment of the invention illustrated in FIG. 2, crystallization is conducted in multiple stirred crystallization vessels 152 and 156 in series and in flow communication for transfer of product slurry from vessel 152 to vessel 156. Cooling in the crystallization vessels is accomplished by pressure release, with the slurry cooled in vessel 152 to a temperature in the range of about 150-190° C. and then further to about 110-150° C. in vessel 156. One or more of the crystallization vessels is vented, as at 154 and 158, respectively, for removal to heat exchange means (not shown) of vapor resulting from pressure let down and generation of steam from the flashed vapor. Vapor removed from one or more upstream crystallization vessels, such as vessel 152, to heat exchange means (not shown) is preferably condensed and liquid condensate comprising water, acetic acid solvent and soluble products and by-products of the oxidation can directed to one or more downstream crystallization vessels, as at 156, to allow for recovery of crystallizable components such as terephthalic acid and oxidation by-products entering and condensed from the flashed vapors from one or more upstream vessel.

Crystallization vessel 156 is in fluid communication with a solid-liquid separation device 190, which is adapted to receive from the crystallization vessel a slurry of solid product comprising terephthalic acid and oxidation by-products in a mother liquor from the oxidation comprising acetic acid and water, and to separate a crude solid product comprising terephthalic acid and by-products from the liquid. Separation device 190 is a centrifuge, rotary vacuum filter or pressure filter. In preferred embodiments of the invention, the separation device is a pressure filter adapted for solvent exchange by positive displacement under pressure of mother liquor in a filter cake with wash liquid comprising water. The oxidation mother liquor that results from the separation exits separation device 190 in stream 191 for transfer to mother liquor drum 192. A major portion of the mother liquor is transferred from drum 192 to oxidation reactor 110 for return to the liquid phase oxidation reaction of acetic acid, water, catalyst and oxidation reaction by-products dissolved or present as fine solid particles in the mother liquor. Crude solid product comprising terephthalic acid and impurities comprising oxidation by-products of the para-xylene feedstock is conveyed, with or without intermediate drying and storage, from separation device 190 to purification solution make up vessel 202 in stream 197. The crude solid product is slurried in make up vessel 202 in purification reaction solvent, all or at least a portion, and preferably about 60 to about 100 wt. %, of which, comprises condensate liquid from off-gas treatment section 300 recovered by condensation in condensing zones 350 of pressurized gas removed from separation device 330 and directed in series to condensers 352 and 362. If used, make up solvent, such as fresh demineralized water or suitable recycle streams such as liquid condensed from vapors resulting from pressure letdown in crystallization of purified terephthalic acid product as discussed below, can be directed to make up tank 202 from vessel 204. Slurry temperature in the make up tank preferably is about 80 to about 100° C.

Crude product is dissolved to form a purification reaction solution by heating, for example to about 260 to about 290° C. in makeup tank 202 or by passage through heat exchangers (not shown) as it is transferred to purification reactor 210. In reactor 210, the purification reaction solution is contacted with hydrogen under pressure preferably ranging from about 85 to about 95 kg/cm$^2$.

A portion of the purification liquid reaction mixture is continuously removed from hydrogenation reactor 210 in stream 211 to crystallization vessel 220 where terephthalic acid and reduced levels of impurities are crystallized from the reaction mixture by reducing pressure on the liquid. The resulting slurry of purified terephthalic acid and liquid formed in vessel 220 is directed to solid-liquid separation apparatus 230 in stream line 221. Vapors resulting from pressure letdown in the crystallization reactor can be condensed by passage to heat exchangers (not shown) for cooling and the resulting condensate liquid redirected to the process, for example as recycle to purification feed makeup tank 202, through suitable transfer lines (not shown). Purified terephthalic acid exits solid-liquid separation device 230 in stream 231. The separation device can be a centrifuge, rotary vacuum filter, a pressure filter or combinations of one or more thereof. Condensate liquid recovered in condensing means 350 can be directed to the separation device as wash liquid for separation to replace or reduce demineralized water requirements for final washing of the purified product.

Purification mother liquor from which the solid purified terephthalic acid product is separated in solid-liquid separator 230 comprises water, minor amounts of dissolved and suspended terephthalic acid and impurities including hydrogenated oxidation by-products dissolved or suspended in the mother liquor. According to the preferred process embodiment illustrated in FIG. 2, at least a portion, and preferably all or substantially all, of the purification mother liquor is directed in stream 233 to oxidation reaction off-gas treatment system 300 where it is introduced to high pressure distillation column 330 used for separation of water and solvent acetic acid in a high pressure vapor removed from oxidation reactor 110. The purification mother liquor directed to column 330 is introduced to the column at an upper portion thereof, as at 336, to provide liquid reflux for separation. Transfer of purification mother liquor from solid-liquid separation device 230 to the high pressure distillation column also allows for recycle of terephthalic acid and impurities in the mother liquor to oxidation reactor 110 where they are oxidized or converted to terephthalic acid, while water content of the purification mother liquor substantially vaporizes in the distillation column, exiting in a pressurized gas removed from column, without significantly impacting water balance in oxidation. Transfer of purification mother liquor from solid-liquid separation device 230 to the distillation column also reduces the volume of liquid effluent that needs to be directed to liquid waste treatment and provides for return of valuable terephthalic acid to oxidation and, in turn, removal thereof for recovery in oxidation crystallizers 152 and 156.

Reaction off-gas generated by the liquid phase oxidation of para-xylene feedstock in reactor vessel 110 is removed from the reactor through vent 116 and directed in stream 111 to separation device 330 which, in the embodiments represented in FIG. 2, is a high pressure distillation column having a plurality of trays preferably providing about 30 to about 50 theoretical plates and is supplied with liquid for reflux through liquid inlet 336. The vapor stream from oxidation is introduced to column 330 preferably at temperature and under pressure of about 150 to about 225° C. and about 4 to about 21 kg/cm² gauge, respectively, and not substantially less than in oxidation reactor 110. As described above, FIG. 2 illustrates a preferred embodiment of the invention in which a portion of the reflux liquid introduced to the column comprises purification mother liquor from which solid purified terephthalic acid is separated in solid-liquid separation device 230. Column 330 includes, for example, 80 trays (not shown). In the embodiment depicted in the Figure, about 50 to about 80 of the trays are disposed below reflux inlet 336 for substantial separation of solvent acetic acid and water in the high pressure off gas from oxidation introduced into the column. As discussed further below, about 10 to about 30 additional trays are positioned above reflux inlet 336 but below introduction of a second reflux liquid 344 for washing of oxidation by-products out of the vapor phase in the column.

As depicted in FIG. 2, distillation column 330 also includes, as a preferred though optional feature, at least one additional reflux liquid inlet as at 344 for supply of a portion of the total reflux, and preferably about 30 to about 70% of the volumetric flow, to the column. Inlet 344 is positioned so that the additional reflux liquid supplied to the column is introduced at a location that is separated from reflux inlet 336 by trays corresponding to one or more theoretical equilibrium stages, and preferably about 2 to about 10 such stages. In the figure, inlets 336 and 344 preferably are separated by about 10 to about 30 trays. Additional reflux to the column can be supplied from the same or different sources as reflux supplied at inlet 336, such as mother liquor from recovery of solid comprising a pure form of aromatic carboxylic acid from a purification liquid reaction mixture or, as in the embodiment of FIG. 2, a portion of condensate liquid recovered by condensation of a high pressure gas from distillation column 330 in condensing zone 350. In the configuration illustrated in FIG. 2, the reflux supplied to the column 330 at inlet 344 has trays providing equilibrium stages above it which allow washing of para-xylene oxidation by-products including hydrogenated derivatives thereof introduced in purification mother liquor reflux, such as p-toluic acid and benzoic acid, down the tower into the oxidation reactor 110 via stream 331.

Water and solvent acetic acid vapors in the high pressure vapor phase introduced to the distillation column are separated, such that an acetic acid-rich, water-lean liquid phase and a separator exit gas under pressure are formed. At least 95 wt. % of the acetic acid in the high pressure vapor from oxidation is separated into the liquid phase. The liquid phase preferably comprises about 60 to about 85 wt % acetic acid and preferably no more than about 25 wt. % water. It also comprises minor amounts of other components less volatile than the acetic acid, such as terephthalic acid and para-xylene oxidation by-products such as p-toluic acid and benzoic acid introduced with the purification mother liquor reflux and may also include other components such as solvent by-products from oxidation. A high pressure gas from the separation primarily comprises water vapor and also contains unreacted oxygen gas, minor amounts of solvent acetic acid vapors, unreacted para-xylene, oxidation by-products, carbon oxides, and nitrogen introduced from the air used as the oxygen source for oxidation.

Liquid phase resulting from separation in distillation column 330 exits the column at a lower portion thereof and preferably is returned directly or indirectly to oxidation reactor 110, as in stream 331. Return of the liquid phase to oxidation provides make up solvent acetic acid to the oxidation reaction and can reduce feedstock loss by allowing for conversion to desired products of by-products condensed from the oxidation vapor phase as well as those recycled from purification mother liquor reflux to the column.

High pressure gas resulting from separation of water and acetic acid vapors in distillation column 330 is removed from the column and directed to condensing means 350, which as depicted in FIG. 2, includes condensers 352 and 362, and disengagement drum 372. Preferably, condensation is conducted such that liquid condensate water at a temperature of about 40 to about 60° C. is recovered in at least one stage. In the embodiment illustrated in the figure, condensation is conducted by indirect heat exchange in condensing means 352 with water at a temperature of about 120 to about 170° C., with effluent from the condenser 352 directed to condenser 362 in stream 361 for condensation using cooling water at about 30 to about 40° C. Gas and liquid effluent from condenser 362 is directed in stream 363 to drum 372 in which condensate liquid comprising water is collected and removed in stream 373 and from which a condenser exhaust gas under pressure is withdrawn as stream 375. Condensate liquid recovered from the pressurized exit gas from distillation column 330 by condensation in condensing means 350 is at least about 95 wt. % water and also comprises minor amount of organic impurities. The condensate liquid is transferred in stream 373 to one or more vessels or liquid receptacles used in or for the purification steps. In the embodiment illustrated in FIG. 2, at least a portion, and preferably a substantial portion, of the condensate liquid is transferred to purification solution make up tank 202 for use in forming the crude product slurry and purification reaction solution that is directed to purification reactor 210. Other purification vessels and liquid receiving equipment and uses to which the condensate liquid can be directed include crystallization vessel 220 for use as clean make-up solvent to replace purification reaction liquid vaporized in the crystallizer and solid liquid separation device 230 for use as wash liquid or seal flush. The condensate liquid also is suitable for uses outside purification, such as reflux to distillation column 330 and wash liquid for solvent exchange filters used for separating solid products recovered from oxidation from oxidation mother liquor.

Water used as heat exchange fluid for condensation of pressurized gas from distillation column 330 is heated by heat exchange in condensing means 350 to form pressurized steam which can be directed to an energy recovery device such as steam turbine 450 in the process embodiment depicted in FIG. 2. As described above with reference to FIG. 1, condensation of pressurized gas from separation of solvent acetic acid and water in the high pressure vapor phase from oxidation can be conducted using two or more condensers in series using heat exchange fluids at successively lower temperatures. In such embodiments, steam generated from condensation at decreasing temperatures is under decreasing pressures, thereby allowing for efficiencies in use of steam at the different pressures by matching with differing heat or energy inputs to operations in which steam is used.

Uncondensed exhaust gas from condensation removed in stream 375 comprises incondensable components such as unconsumed oxygen from oxidation, nitrogen from the air used as oxygen source to the oxidation, carbon oxides from such air as well as from reactions in oxidation, and traces of unreacted para-xylene and its oxidation by-products, methyl acetate and methanol, and methyl bromide formed from the bromine promoter used in oxidation. In the embodiment illustrated in the figure, the uncondensed gas is substantially free of water vapor owing to substantially complete condensation into the condensate liquid recovered in the condensing means.

Uncondensed exhaust gas from condensing means 350 is under pressure of about 10 to about 15 kg/cm$^2$ and can be transferred directly to a power recovery device or to a pollution control device for removing corrosive and combustible species in advance of power recovery. As depicted in FIG. 2, uncondensed gas is first directed to treatment to remove unreacted feed materials and traces of solvent acetic acid and/or reaction products thereof remaining in the gas. Thus, uncondensed gas is transferred in stream 375 to high pressure absorber 380 for stripping para-xylene, acetic acid, methanol and methyl acetate without substantial loss of pressure. Absorption tower 380 is adapted for receipt of the substantially water-depleted gas remaining after condensation and for separation of para-xylene, solvent acetic acid and its reaction products from oxidation from the gas by contact with one or more liquid scrubbing agents. A preferred absorber configuration, illustrated in the figure, comprises tower 380 having a plurality of internally disposed trays or beds or structured packing (not shown) to provide surface for mass transfer between gas and liquid phases. Inlets (not shown) for addition of scrubbing agent to the absorber in streams 381 and 383, respectively, are disposed at one or more upper, and one or more lower portions of the tower. The absorber also includes an upper vent 382 from which a scrubbed gas under pressure comprising incondensable components of the inlet gas to the absorber is removed via line 385 and a lower outlet 384 for removal of a liquid acetic acid stream into which components from the gas phase comprising one or more of para-xylene, acetic acid, methanol and/or methyl acetate have been scrubbed. A bottoms liquid is removed from a lower portion of the tower and can be directed to reactor 110 for reuse of recovered components.

Pressurized gas removed from condensing means 350 or, in embodiments as depicted in FIG. 2, from the vent 382 from the high pressure absorber, can be directed to pollution control means, as at 390, for conversion of organic components and carbon monoxide in the pressurized gas from the condenser or the absorber to carbon dioxides and water. A preferred pollution control means is a catalytic oxidation unit adapted for receiving the second pressurized gas, optionally heating it to promote combustion and directing the gas into contact with a high temperature-stable oxidation catalyst disposed on a cellular or other substantially porous support such that gas flow through the device is substantially unaffected. Overhead gas from absorber 380 is directed to pollution control system 390 which includes preheater 392 and catalytic oxidation unit 394. The gas is heated to about 250 to 450° C. in the preheater and passed under pressure of about 10 to 15 kg/cm$^2$ to oxidation unit 394 where organic components and by-products are oxidized to compounds more suited for beneficial environmental management.

An oxidized high pressure gas is directed from catalytic oxidation unit 394 to expander 400 which is connected to generator 420. Energy from the oxidized high pressure gas is converted to work in the expander 400 and such work is converted to electrical energy by generator 420. Expanded gas exits the expander and can be released to the atmosphere, preferably after caustic scrubbing and/or other treatments for appropriately managing such releases.

That which is claimed is:

1. A process for manufacture of aromatic carboxylic acid comprising
   (a) contacting in a reaction zone a feed material comprising at least one aromatic hydrocarbon precursor to the acid with gaseous oxygen in a liquid phase reaction mixture comprising monocarboxylic acid solvent and water and in the presence of a catalyst comprising at least one heavy metal component to form
      (i) an effluent comprising an aromatic carboxylic acid and impurities comprising oxidation by-products of the aromatic hydrocarbon precursor dissolved or suspended in the liquid effluent, and
      (ii) a high pressure vapor phase comprising solvent monocarboxylic acid, water and minor amounts of the aromatic hydrocarbon precursor and by-products;
   (b) separating in a separation zone a monocarboxylic acid solvent and water from the high pressure vapor phase from step (a) to form a solvent monocarboxylic acid-rich, water lean liquid and a high pressure gas comprising water vapor;
   (c) condensing in a condensing zone the high pressure gas from step (b) to form a condensate liquid comprising water substantially free of organic impurities;
   (d) purifying the effluent from step (a) in a purification zone to form purified aromatic carboxylic acid and a purification mother liquor comprising water and impurities;

(e) directing at least a portion of the purification mother liquor from step (d) to a first inlet into the separation zone as reflux; and (f) directing at least a portion of the condensate liquid from step (c) to the separation zone at a second inlet into the separation zone as reflux;

wherein the first inlet is separated from the second inlet by at least one tray corresponding to at least one equilibrium stage.

2. The process of claim 1 wherein the aromatic carboxylic acid comprises terephthalic acid and an aromatic hydrocarbon precursor is para-xylene.

3. The process of claim 1 additionally comprising recovering energy from the condensing zone exhaust gas from a condensing zone.

4. The process of claim 1 wherein energy is recovered as work.

5. The process of claim 3 wherein the high pressure gas removed from a separation zone is condensed in a condensing zone by indirect heat exchange with a heat exchange fluid comprising water to generate steam at one or more pressures.

* * * * *